United States Patent [19]
Van Dorsselaer et al.

[11] Patent Number: 5,948,778
[45] Date of Patent: *Sep. 7, 1999

[54] DIFLUORO STATONE ANTIVIRAL ANALOGS

[75] Inventors: Viviane Van Dorsselaer, Strasbourg; Daniel Schirlin, Lampertheim; Céline Tarnus, Strasbourg, all of France

[73] Assignee: Merrel Pharmaceuticals Inc., Bridgewater, N.J.

[ * ] Notice: This patent is subject to a terminal disclaimer.

[21] Appl. No.: 09/081,307

[22] Filed: May 19, 1998

Related U.S. Application Data

[63] Continuation of application No. 08/596,336, filed as application No. PCT/US94/09053, Aug. 10, 1994, Pat. No. 5,831,094.

[30] Foreign Application Priority Data

Sep. 9, 1993 [EP] European Pat. Off. .............. 93402194

[51] Int. Cl.$^6$ ...................... A61K 31/535; A61K 31/165; C07C 237/52; C07D 265/30
[52] U.S. Cl. .................................... 514/237.8; 514/231.8; 514/237.2; 514/237.5; 514/307; 514/314; 514/318; 514/332; 514/357; 514/394; 514/466; 514/486; 514/539; 514/616; 514/619; 514/620; 544/78; 544/82; 544/131; 544/168; 546/146; 546/170; 546/194; 546/265; 546/335; 546/336; 546/337; 548/309.7; 549/441; 560/27; 564/137; 564/138; 564/153; 564/165
[58] Field of Search ................................ 544/78, 82, 131, 544/168; 546/145, 170, 335, 337, 194, 265, 336; 549/441; 560/27; 564/137, 138, 165, 153; 514/237.5, 307, 314, 357, 466, 486, 619, 620, 231.8, 237.2, 237.8, 318, 332, 394, 539, 616; 548/309.7

[56] References Cited

U.S. PATENT DOCUMENTS

| | | | |
|---|---|---|---|
| 5,066,643 | 11/1991 | Abeles et al. | 514/18 |
| 5,559,140 | 9/1996 | Schirlin et al. | 514/357 |

FOREIGN PATENT DOCUMENTS

| | | |
|---|---|---|
| 2098020 | 3/1992 | Canada . |
| 0275101 | 7/1988 | European Pat. Off. . |
| 0352000 | 1/1990 | European Pat. Off. . |
| 0386611 | 9/1990 | European Pat. Off. . |
| 2171103 | 8/1986 | United Kingdom . |
| 2196958 | 5/1988 | United Kingdom . |
| 2203740 | 10/1988 | United Kingdom . |
| 2212158 | 7/1989 | United Kingdom . |
| 8606379 | 11/1986 | WIPO . |
| 9000399 | 1/1990 | WIPO . |
| 9212123 | 7/1992 | WIPO . |
| 9217176 | 10/1992 | WIPO . |
| 9319059 | 9/1993 | WIPO . |
| 9323373 | 11/1993 | WIPO . |
| 9323379 | 11/1993 | WIPO . |
| 9501958 | 1/1995 | WIPO . |
| 9602499 | 2/1996 | WIPO . |

OTHER PUBLICATIONS

Journ. Of Med. Chem. vol. 29, No. 10, pp. 2080–2087 (1986)–S. Thaisrivongs et al. "Design and Synthesis of potent and Specific Renin Inhibitors Containing Difluorostatine, Difluorostatone and Related Analoges".

Journ. Of Med. Chem. vol. 35, No. 1, pp. 2–14 (1992)–A.M. Doherty et al. "Design and Synthesis of Potent, Selective and Orally Active Fluorine Containing Renin Inhibitors".

*Primary Examiner*—Richard L. Raymond
*Attorney, Agent, or Firm*—Mark C. Nelligan

[57] ABSTRACT

This invention relates to novel statone antiviral analogs, to the processes and intermediates useful for their preparation and to their use as antiviral agents.

24 Claims, No Drawings

DIFLUORO STATONE ANTIVIRAL ANALOGS

This is a continuation of application Ser. No. 08/596,336, filed Feb. 20, 1996, now U.S. Pat. No. 5,831,094 which is a 371 of PCT/US94/09053, filed Aug. 10, 1994, which are herein incorporated by reference.

This invention relates to novel statone antiviral analogs, to the processes and intermediates useful for their preparation and to their use as anti-viral agents.

BACKGROUND OF THE PRESENT INVENTION

Retroviruses are a class of viruses which transport their genetic material as ribonucleic acid rather than as deoxyribonucleic acid. Retroviruses are associated with a wide variety of diseases in man, one of which is AIDS. Although there have been disclosures of other anti-viral agents useful in the treatment of AIDS, for example see patent applications EP 0 218 688, EP 0 352 000 and PCT/US 91/09741, the compounds of the present invention have not been previously disclosed. PCT/US 91/09741 is hereby incorporated by reference.

DESCRIPTION OF THE PRESENT INVENTION

More specifically this invention relates to novel difluoro statone analogs of Formula 1

$$R_1\left[\underset{\underset{O}{\|}}{C}NHCH\underset{P_2}{|}\right]_x \underset{\underset{O}{\|}}{C}NHCHC\underset{P_1}{|}\underset{\underset{O}{\|}}{-}CF_2C\underset{\underset{O}{\|}}{-}NR_5R_6 \qquad I$$

and the stereoisomers, hydrates, isosteres and the pharmaceutically acceptable salts thereof wherein $P_1$ is $$C_{1\text{-}6}\,\text{alkylene}\!-\!\!\!\bigcirc\!\!\!\overset{T}{\underset{T'}{\diagdown}},$$

wherein
T is $[(O)_b—W—R]$ and T' is $[(O)_b{'}—W'—R']$ or H, wherein each of W and W' are independently $C_{1-6}$ alkylene or nothing,
provided that W is $C_{2-6}$ alkylene when W is directly attached to a nitrogen atom in R,
provided that W' is $C_{2-6}$ alkylene when W' is directly attached to a nitrogen atom in R';
$P_2$ is $C_{1-6}$ alkyl, cyclopentyl, hydroxy $C_{1-6}$ alkyl, phenyl, benzyl or 3-tetrahydrofuryl;
R and R' are each independently $C_{2-6}$ alkenylene, piperazinyl, substituted piperazinyl, piperidyl, morpholinyl, pyridyl, pyrazinyl, or pyrimidinyl, wherein substituted piperazinyl is piperazinyl substituted on one nitrogen atom thereof with CHO, C(O)NHR$_4$, $C_{1-4}$ alkyl or $CO_2R_4$;
$R_1$ is benzyloxy, $C_{1-6}$ alkoxy, $C_{1-6}$ alkyl, phenyl, benzyl, phenethyl, fluorenylmethylenoxy, 2-quinolinyl, PDL, $$\underset{\phantom{X}}{CH_2N\!\!-\!\!(CH_2)_3CH_2}, \qquad \underset{\phantom{X}}{O\!\!-\!\!(CH_2)_2\!\!-\!\!N\!\!-\!\!CH_2CH_2},$$

$NHSO_2R_4$, $N(R_4)$(benzyl), or $N(R_4)$(PDL);

PDL is —$(CH_2)_a$-2-, 3-, or 4-pyridyl, or 2-substituted benzyloxy, wherein the substitution is with a nitro, OH, amino, $C_{1-6}$ alkoxy, hydroxy $C_{1-6}$ alkylene, or halogeno;

$R_3$ is $C_{1-6}$ alkenyl, $C_{1-6}$ alkoxy, hydroxy $C_{1-6}$ alkyl, $C_{1-6}$ alkyl, or OH;

$R_4$ is H, $C_{1-6}$ alkyl, phenyl or benzyl;

$R_5$ is H, $C_{1-6}$ alkyl, OH, $C_{1-6}$ alkoxy, $$-\!(CH_2)_d\!\!-\!\!\bigcirc\!\!-\!\!(V)_e,$$

$CH_2Si(CH_3)_2(R_3)_2$, $(CH_2)_d$—(dimethoxyphenyl)—$(CH_2)_{d'}$, PDL,

—N—$(CH_2)_2$—O—$CH_2CH_2$, $$HO\!\!-\!\!\!\overset{(CH_2)_b}{\diagup}\!\!-\!\!\text{indanyl},\quad CH_2\!\!-\!\!\text{benzimidazolyl},$$

—($C_{1-6}$ alkylene)—$OR_4$ or —$CH(Y)(Z)$,

Y being $C_{1-6}$ hydroxy alkylene, $C_{1-6}$ alkyl, or $(CH_2)_e—C_6H_4—(V)_e$, and Z being CHO, $CO_2R_4$, $CO_2NHR_4$ or $(CH_2)_e—OR_4$, and V being $OR_4$ or hydroxy $C_{1-6}$ alkylene;

$R_6$ is as defined for $R_5$ with the proviso that $R_6$ is other than H when $R_5$ is H, and when $R_5$ and $R_6$ are taken together with nitrogen atom to which they are attached form a heterocyclic moiety of the formulae (a) —N(CH$_2$)$_3$CH$_2$, (b) —N(CH$_2$)$_4$CH$_2$, (c) —N(CH$_2$)$_2$OCH$_2$CH$_2$, (d) tetrahydroisoquinolinyl, -continued

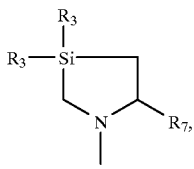
(e)

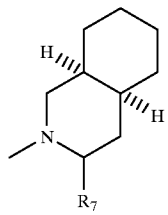
(f)

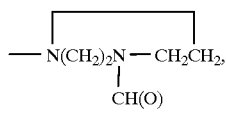
(g)

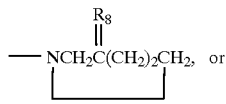
(h)

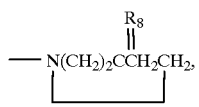
(i)

$R_7$ is $CH_2OR_4$ or $C(O)NHR_4$, CHO, $R_8$ is (H,OH) or =O;

a is zero, 1, 2 or 3;

b and b' are each independently zero or 1;

d and d' are each independently 1 or 2;

e and e' are each independently zero, 1 or 2; and x is zero or one.

Isosteres of the compounds of Formula I include those wherein (a) the α-amino acid residues of the $P_1$ and $P_2$ substituents are in their unnatural configuration (when there is a natural configuration) or (b) when the normal peptidic carbamoyl linkage is modified, such as for example, to form —$CH_2NH$— (reduced),

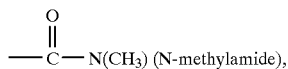

—$COCH_2$— (keto), —$CH(OH)CH_2$— (hydroxy), —$CH(NH_2)CH_2$— (amino), —$CH_2CH_2$— (hydrocarbon). Preferably a compound of the invention should not be in an isosteric form. Unless otherwise stated the α-amino acids are preferably in their L-configuration.

A compound of the invention may be in free form, e.g., amphoteric form, or in salt, e.g., acid addition or anionic salt, form. A compound in free form may be converted into a salt form in an art-known manner and vice-versa.

The pharmaceutically acceptable salts of the peptide of Formula I (in the form of water, or oil-soluble or dispersible products) include the conventional non-toxic salts or the quaternary ammonium salts of these peptides, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethane-sulfonate, lactate, maleate, methanesulfonate, 2-naphthalenesulfonate, nicotinate, oxalate, paemoate, pectinate, persulfate, 3-phenylpropionate, picrate, pivalate, propionate, succinate, tartrate, thiocyanate, tosylate, and undecanoate. Base salts include ammonium salts, alkalimetal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The hydrates of the compounds of Formula I are hydrated compounds having the partial structure

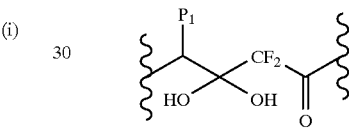

and in their end-use application are generally the active forms.

In general, as used herein, the term "alkyl" includes the straight, branched-chain and cyclized manifestations thereof unless otherwise indicated, particularly such moieties as methyl, ethyl, isopropyl, n-butyl, t-butyl, —$CH_2$-t-butyl, cyclopropyl, n-propyl, pentyl, cyclopentyl, n-hexyl, cyclohexyl and cyclohexylmethyl. The term "aralkyl", when used, includes those aryl moieties attached to an alkylene bridging moiety, preferably methyl or ethyl.

"Aryl" includes both carbocyclic and hetereocyclic moieties of which phenyl, pyridyl, pyrimidinyl, pyrazinyl, indolyl, indazolyl, furyl and thienyl are of primary interest; these moieties being inclusive of their position isomers such as, for example, 2-, 3-, or 4-pyridyl, 2- or 3-furyl and thienyl, 1-, 2-, or 3-indolyl or the 1- and 3-indazolyl, as well as the dihydro and tetrahydro analogs of the furyl and thienyl moieties. Also included within the term "aryl" are such fused carbocyclic moieties as pentalenyl, indenyl, naphthalenyl, azulenyl, heptalenyl, acenaphthylenyl, fluorenyl, phenalenyl, phenanthrenyl, anthracenyl, acephenanthrylenyl, aceanthrylenyl, triphenylenyl, pyrenyl, chrysenyl and naphthacenyl. Also included within the term "aryl" are such other heterocyclic radicals as 2- or 3-benzo[b]thienyl, 2- or 3-naphtho[2,3-b]thienyl, 2- or 3-thianthrenyl, 2H-pyran-3-(or 4- or 5-)yl, 1-isobenzofuranyl, 2H-chromenyl-3-yl, 2- or 3-phenoxathiinyl, 2- or 3-pyrrolyl, 4- or 3-pyrazolyl, 2-pyrazinyl, 2-pyrimidinyl, 3-pyridazinyl, 2-indolizinyl, 1-isoindolyl, 4H-quinolizin-2-yl, 3-isoquinolyl, 2-quinolyl, 1-phthalazinyl, 1,8-naphthyridinyl, 2-quinoxalinyl, 2-quinazolinyl, 3-cinnolinyl, 2-pteridinyl, 4aH-carbazol-2-yl, 2-carbazolyl, β-carbolin-3-yl, 3-phenanthridinyl, 2-acridinyl, 2-perimidinyl, 1-phenazinyl, 3-isothiazolyl, 2-phenothiazinyl, 3-isoxazolyl, 2-phenoxazinyl, 3-isochromanyl, 7-chromanyl, 2-pyrrolin-3-yl, 2-imidazolidinyl, 2-imidazolin-4-yl, 2-pyrazolidinyl, 3-pyrazolin-3-yl, 2-piperidyl, 2-piperazinyl, 1-indolinyl, 1-isoindolinyl, 3-morpholinyl, benzo[b]isoquinolinyl and benzo[b]furanyl, including the position isomers thereof except that the heterocyclic moieties cannot be attached directly through their nitrogen one, two or three substituents independently selected from $C_{1-6}$ alkyl, haloalkyl, alkoxy, thioalkoxy, aminoalkylamino, dialkylamino, hydroxy, halo, mercapto, nitro, carboxaldehyde, carboxy, carboalkoxy and carboxamide.

Likewise the term "alkylene" (a divalent alkane radical) includes straight or branched-chain moieties. Some examples of branched-chain alkylene moieties are ethylethylene, 2-methyltrimethylene, 2,2-dimethyltrimethylene, and so on. For example, $C_3$ alkylene can mean

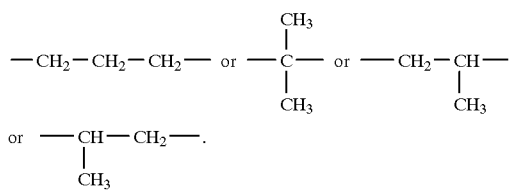

All ($C_{1-6}$) moieties such as $C_{1-6}$ alkyl, $C_{1-6}$ alkylene, $C_{2-6}$ alkenylene, $C_{1-6}$ alkoxy, and hydroxy $C_{1-6}$ alkyl, are more preferably $C_{13}$ moieties (containing 1–3 carbon atoms instead of 1–6 carbon atoms, more preferably a $C_{1-2}$ moiety and most preferably a $C_1$ moiety). "Alkenylene" (divalent unsaturated moiety) can also mean "Alkenyl" such as ethenyl (univalent unsaturated moiety).

The fluorenylmethyloxy moiety is that moiety generally called by its abbreviation FMOC, and is the fluorenyl moiety bearing —CH$_2$O attached to the 9-position of the fluoroenyl moiety. Other terms defined herein are

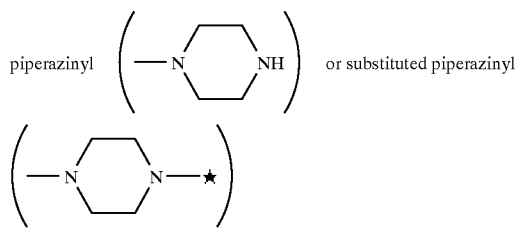

the substitution (★) occurring only at one nitrogen molecule which is not attached to the remainder of the molecule (attachment via a nitrogen atom). The substituents are one of CHO, C(O)NHR$_4$, $C_{1-4}$ alkyl or CO$_2$R$_4$. Piperidyl and morpholinyl both bind to the rest of the

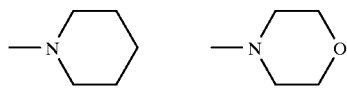

molecule via their respective nitrogen atoms while pyrimidinyl, pyridyl and pyrazinyl bind to the rest

of the molecule anywhere except their respective nitrogen atoms.

More specifically, in the instance wherein P$_2$ is either $C_{1-6}$ alkyl or hydroxy $C_{1-6}$ alkyl, such moieties as —C(CH$_3$)$_3$, —CH(CH$_3$)$_2$, —CH(CH$_3$)(C$_2$H$_5$), —C(OH)(CH$_3$)$_2$ and —CH(OH)CH$_3$ are preferred. The "hydroxy $C_{1-6}$ alkyl" moiety is illustrated in one example by —CH$_2$—OH, the "$C_{1-6}$ alkoxy $C_{1-6}$ alkyl" moiety, is illustrated in one example by —CH$_2$—OCH$_3$, (although in each instance the $C_{1-6}$ alkylene may be straight or branched and the hydroxy radical is not limited to the terminal carbon atom of the alkyl moiety).

As it is often quite advantageous to have what is termed an amino protecting group (Pg), the scope of those compounds of Formula I, includes those R$_1$ moieties which, together with their adjacent carbonyl moiety form such groups as acetyl (Ac), succinyl (Suc), benzoyl (Bz), t-butyloxycarbonyl (Boc), benzyloxycarbonyl (CBZ), tosyl (Ts), dansyl (DNS), isovaleryl (Iva), methoxysuccinyl (MeOSuc), 1-adamantanesulphonyl (AdSO$_2$), 1-adamantaneacetyl (AdAc), phenylacetyl, t-butylacetyl (Tba), bis[(1-naphthyl)methyl]acetyl (BNMA) and Rz wherein Rz is an aryl group as previously described suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolo, and acylsulfonamido (i.e., acylaminosulfonyl and sulfonylaminocarbonyl) containing from 1 to 15 carbons, provided that when the acylsulfonamido contains an aryl. The aryl may be further substituted by a member selected from fluoro, chloro, bromo, iodo and nitro.

In those instances wherein there is an Rz moiety, it is preferred that Rz represent acylsulfonamido, particularly those wherein the acylsulfonamido contains an aryl moiety (preferably phenyl) substituted by a halogen. The preferred Rz moieties being 4-[(4-chlorophenyl) sulfonylaminocarbonyl]phenylcarbonyl, 4-[(4-bromophenyl)sulfonylamino carbonyl]-phenylcarbonyl and 4-[phenylsulfonylamino carbonyl]-phenylcarbonyl (said moieties being abbreviated as 4-Cl-ø-SAC-Bz, 4-Br-ø-SAC-Bz and ø-SAC-Bz, respectively).

Among the classes of amino protecting groups contemplated are: (1) acyl type protecting groups such as formyl, trifluoroacetyl, phthalyl, p-toluenesulfonyl (tosyl), benzenesulfonyl, nitrophenylsulfenyl, tritylsulfenyl, O-nitrophenoxyacetyl, and α-chlorobutyryl; (2) aromatic urethane type protecting groups such as benzyloxycarbonyl and substituted benzyloxycarbonyls such as p-chlorobenzyloxycarbonyl, p-methoxybenzyloxycarbonyl, p-nitrobenzyloxycarbonyl, p-bromobenzyloxycarbonyl, 1-(p-biphenylyl)-1-methylethoxycarbonyl, α-,α-dimethyl-3,5-dimethoxybenzyloxycarbonyl, and benzhydryloxycarbonyl; (3) aliphatic urethane protecting groups such as tert-butyloxycarbonyl (Boc), diisopropylmethoxycarbonyl, isopropyloxycarbonyl, ethoxycarbonyl, and allyloxycarbonyl; (4) cycloalkyl urethane type protecting groups such as cyclopentyloxycarbonyl, adamantyloxycarbonyl, and cyclohexyloxycarbonyl; (5) thio urethane type protecting groups such as phenylthiocarbonyl; (6) alkyl type protecting groups such as triphenylmethyl (trityl) and benzyl (Bzl); (7) tri-alkylsilane protecting groups such as trimethylsilane if compatible. The preferred α-amino protecting groups are tert-butyloxycarbonyl (Boc) or benzyloxycarbonyl (CBZ). The use of Boc as an α-amino protecting group for amino acids is described by Bodansky et al. in "The Practice of Peptide Synthesis", Springer-Verlag, Berlin (1984), p. 20.

In general the compounds of this invention may be prepared using standard chemical reactions analogously known in the art.

In the instance wherein it is desired to prepare compounds of the formula

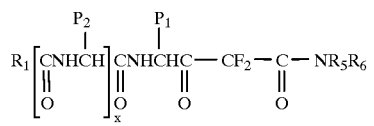

I wherein $R_1$, $P_2$, $P_1$, $R_5$ and $R_6$ are as previously defined, the process outlined by the following reaction schemes may advantageously be utilized.

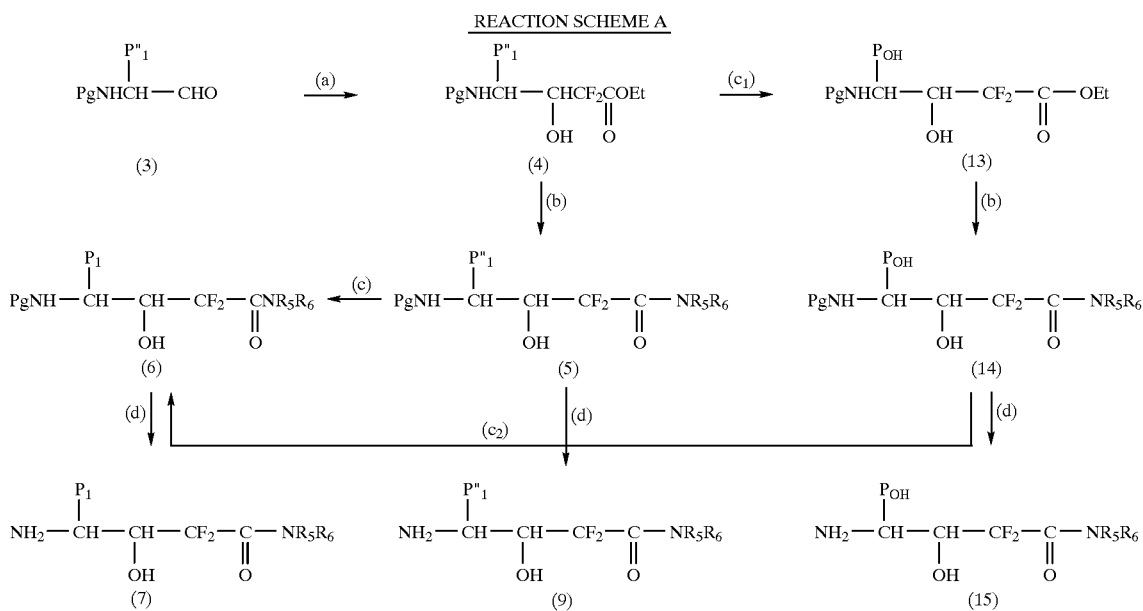

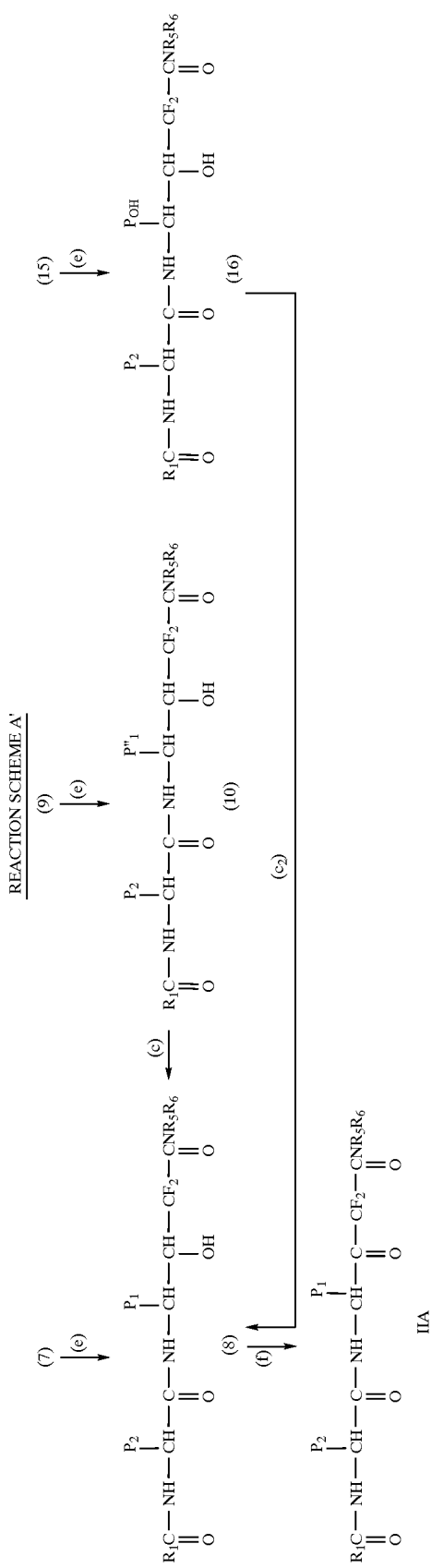

REACTION SCHEME A"

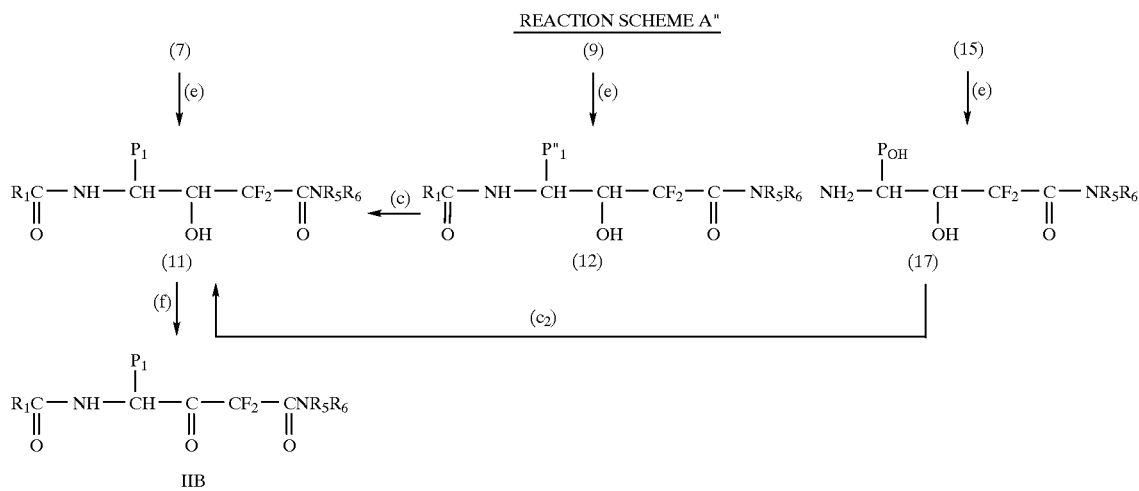

In effecting reaction scheme A, A' or A", the process is initiated by conducting a Reformatsky-type reaction wherein an aldehyde of Formula (3) is subjected to a condensation reaction with an ester of bromodifluoroacetic acid, preferably the ethyl ester in the presence of zinc and in an anhydrous aprotic solvent, e.g., tetrahydrofuran, ether, dimethoxyethane and the like under a nitrogen or argon inert atmosphere. The reaction is gently heated to about 60° C. for about 1–12 hours or ultrasonicated to produce compounds (4).

Step (b) to obtain compounds (5) or (14) may be effected directly or undirectly. In one instance, the esters of Formula (4) or (13) are de-esterified using a strong base (LiOH, KOH, NaOH and the like) in the presence of water using a partially water miscible solvent (such as tetrahydrofuran, dimethoxyethane, dioxane) at about room temperature. The so-obtained de-esterified compound is then aminated with the appropriate $R_5R_6$-substituted amine using a peptide-like coupling procedure—i.e., using a mixed anhydride method using DCC and hydroxybenzotriazole at room temperature in solvents such as $CH_2Cl_2$, tetrahydrofuran or dimethylformamide. Alternatively the esters (4) or (13) may be directly subjected to a reaction with the appropriate $R_5R_6$-substituted amine without or with a solvent (tetrahydrofuran) at about 80° C.

In Step (c) Compounds (6), (8) or (11) are prepared by removal of the $P''_1$ protecting group using standard procedures, e.g., hydrogenation. The free phenol functionality is then reacted with an appropriate alkyl halide in an inert solvent (preferably anhydrous dioxane or anhydrous dimethylformamide) in the presence of a base (potassium or cesium carbonate) with or without potassium iodide at room or reflux temperature.

In Step (c1) compound (13) is prepared by removal of the $P''_1$ protecting group using standard procedures, e.g., hydrogenation, $P_{OH}$ being the compound obtained. $P_{OH}$ being a free phenol.

In Step (c2) compounds (6), (8) or (11) are prepared from the $P_{OH}$ derivatives (14), (16) or (17) by reaction with an appropriate alkylhalide in an inert solvent, in the presence of a base.

In Step (d), for the preparation of Compounds (7), (9) and (15), the protecting groups Pg may readily be removed by standard procedures preferably acid/base hydrolysis (e.g., formic acid at room temperature followed by extraction of the free base after treatment with sodium carbonate).

In Step (e), Compounds (7), (9) or (15) are subjected to a peptide coupling procedure with an appropriately protected acid of the formula $R_1CONHCH(P_2)CO_2H$ or $R_1CO_2H$, using the herein-described procedures (or by any other coupling procedure currently available, or described in European Patent Application, Serial Number 93 401 785.6) to produce compounds (8) and (11) (from compound (7)); (10) and (12) (from compound (9)); and (16) and (17) (from compound (15)).

In Step (f), the oxidation may be effected via the well-known Swern oxidation procedure, or with 1,1,1-tris-(acetyloxy)-1,1-dihydro-1,2-benzodioxol-3(1H)-one. The latter is preferred when more than one basic group is present in the alcohol precursors (8) or (11). The oxidation procedures are effected according to standard procedures well known in the art.

In general the Swern oxidation [see Synthesis, (1981), 165] is effected by reacting about 2 to 20 equivalents of dimethylsulfoxide (DMSO) with about 1 to 10 equivalents of trifluoromethylacetic anhydride $[(CF_3CO)_2O]$ or oxalyl chloride $[(COCl)_2]$, said reactants being dissolved in an inert solvent, e.g., methylene chloride ($CH_2Cl_2$), said reaction being under an inert atmosphere (e.g., nitrogen or equivalently functioning gas) under anhydrous conditions at temperatures of about −70° C. to −30° C. to form an in situ sulfonium adduct to which is added about 1 equivalent of the appropriate alcohols, i.e., compounds (8) and (11). Preferably, the alcohols are dissolved in an inert solvent, e.g., $CH_2Cl_2$, tetrahydrofuran, or minimum amounts of DMSO, and the reaction mixture is allowed to warm to about −50° C. or −20° C. (for about 20–60 minutes) and then the reaction is completed by adding about 3 to 30 equivalents of a tertiary amine, e.g., triethylamine, diisopropylethylamine, N-methyl morpholine, etc.

Another alternative process for converting the alcohols to the desired ketones is an oxidation reaction which employs periodane (i.e., 1,1,1-tris(acetyl)oxy-1,2-benzodioxol-3(1H)-one), [see Dess Martin, J. Org. Chem., 48, 4155, (1983)]. This oxidation is effected by contacting about 1 equivalent of the alcohols with 1 to 5 equivalents of periodane (preferably 1.5 equivalents), said reagent being in suspension in an inert solvent (e.g., methylene chloride) under an inert atmosphere (preferably nitrogen) under anhydrous conditions at 0° C. to 50° C. (preferably room temperature) and allowing the reactants to interact for about 1 to 48 hours. Optional deprotection of the amine protecting groups may be effected as desired after the ketones have been isolated.

In general, the modified Jones oxidation procedure may conveniently be effected by reacting the alcohols with pyridinium dichromate by contacting the reactants together in a water-trapping molecular sieve powder, e.g., a grounded 3 Angstrom molecular sieve), wherein said contact is in the presence of glacial acetic acid at about 0° C. to 50° C., preferably at room temperature followed by isolation and then optionally removing amine protecting groups.

Alternatively, 1 to 5 equivalents of a chromic anhydride-pyridine complex (i.e., a Sarett reagent prepared in situ) [see Fieser and Fieser "Reagents for Organic Synthesis" Vol. 1, pp. 145 and Sarett, et al., J.A.C.S. 25, 422, (1953)] said complex being prepared in situ in an inert solvent (e.g., $CH_2Cl_2$) in an inert atmosphere under anhydrous conditions at 0° C. to 50° C. to which complex is added 1 equivalent of the alcohols allowing the reactants to interact for about 1 to 15 hours, followed by isolation and optionally removing amine protecting groups.

For the preparation of the necessary aldehydes of formula (3), and the preparation of the acids which are to be coupled with the amines of Formula (7), (9) or (15) alternative alkylation procedures are utilized depending upon whether the $P_1$ and/or the $P_2$ moieties are or are not residues of natural amino acids. The preparation of these intermediates wherein the $P_1$ or $P_2$ moieties are residues of natural amino acids (or minor modifications thereof, e.g., $P_1$ or $P_2$ being a benzyl or methyl ether of tyrosine), the compounds are either known or are prepared by processes and techniques well known in the art.

To prepare the intermediates of the formula

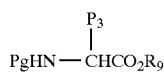

wherein Pg is an amino protecting group, $P_3$ is either a $P'_1$ or $P'_2$ moiety with $P'_1$ and $P'_2$ being as defined for $P_1$ and $P_2$ respectively, except that they are other than residues of naturally occuring amino acids, and the $R_g$ moiety is an alkyl radical, preferably methyl when $P_3$ is $P'_1$, and ethyl when $P_3$ is $P'_2$, alternative methods are available.

To prepare the intermediates of formula

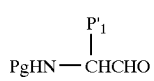 (10B)

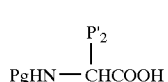 (10A)

the following reaction scheme may be utilized

REACTION SCHEME B

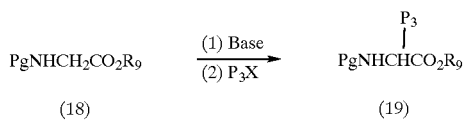

wherein $P_3$ is as previously defined and X is a leaving group, preferably halo or triflate, $R_9$ is methyl when $P_3$ is $P'_1$ and ethyl when $P_3$ is $P'_2$.

In essence, the preparation of compounds (19) utilizes the Krapcho method [Tetrahedron Letters, 26, 2205 (1976)] for alkylation wherein compounds (18) are treated with a base, e.g., LDA, (lithium diisopropylamide), followed by reaction with the desired $P_3X$ in the presence of TMEDA (i.e. tetramethylethylenediamine) in a solvent (tetrahydrofuran) with or without HMPA (i.e. hexamethylphosphoramide) according to the standard Krapcho conditions. Following alkylation the compounds are then subjected to a reduction using diisobutylaluminium hydride (Dibal) in a mixture of solvents, e.g., ether, toluene, hexane, tetrahydrofuran at about −78° C. for about 1 hour. Following the preparation of the aldehydes of Formula (10B), the compounds are subjected to the processes of Reaction Schemes A, A' and/or A".

Alternatively, the compounds of (19) may be prepared by a Malonate/Curtius type sequence of reactions, [see Yamada, et al., J. Amer. Chem. Soc., (1972) 94, 6203] as illustrated by the following reaction scheme

REACTION SCHEME C

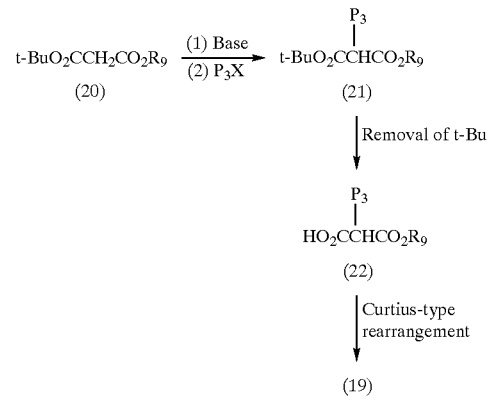

wherein t-Bu is t-butyl, although other selectively removal acid protecting groups may be utilized, and $P_3X$ is as previously defined. This reaction involves the alkylation of the malonate ester (20) followed by selective removal of the t-butyl protecting group to produce compounds (22).

These compounds are then transformed to (19) using the Curtius type rearrangement which entails their conversion to the protected amine via the intermediately formed azides, isocyanates, amines which are then protected with standard amino protecting groups, preferentially being protected in situ.

In the instance wherein $P_3$ represents a $P'_1$ moiety, the ester is transformed to the desired aldehydes of Formula (3) using standard Dibal reduction techniques, particularly in this situation (wherein $P_1$ is not a residue of a natural amino acid). Alternatively, (as is preferred when $P_1$ is a residue of a natural amino acid) the ester is de-esterified to its corresponding acid, converted to its corresponding hydroxamate and the hydroxamate upon treatment with lithium aluminum hydride is converted to its aldehyde. In the instance wherein $P_3$ represents a $P'_2$ moiety, the ethyl ester of compounds (19) are removed and the resulting compounds are ready for coupling as outlined in Reaction Scheme A'.

Having generically described the methods for the preparation of the compounds of this invention, the following specific examples illustrate the chemistry and techniques by which the synthesis may be effected.

The following examples present typical syntheses as described in Schemes A, A' or A". These examples are understood to be illustrative only and are not intended to limit the scope of the present invention in any way. As used herein, the following terms have the indicated meanings: "g" refers to grams; "mmol" refers to millimoles; "ml" refers to milliliters; "bp" refers to boiling point; "mp" refers to melting point; "°C." refers to degrees Celsius; "mm Hg" refers to millimeters of mercury; "μl" refers to microliters; "μg" refers to micrograms; and "μM" refers to micromolar; "Cbz" means carbobenzyloxy.

EXAMPLE 1

4-(N-Benzyloxycarbonyl-L-Valyl)Amino-2,2-Difluoro-3-Oxo-5[4(2-{N-Morpholinyl}Ethyloxy)Phenyl]N-Benzyl Pentanamide

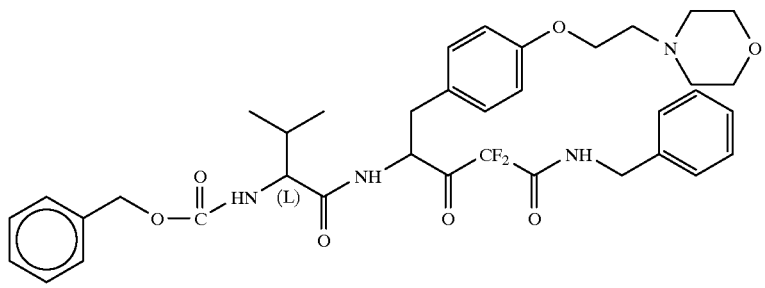

Step A:
4-Tert-Butoxycarbonylamino-2,2-Difluoro-3-Hydroxy-5[4-Benzyloxy)Phenyl]N-Benzyl Pentanamide To a solution of 4-tert-butoxycarbonylamino-2,2-difluoro-3-hydroxy-5-[(4-benzyloxy)phenyl]pentanoic acid, ethyl ester, compound described in Patent Application PCT/US91/09741, filed Dec. 20, 1991 incorporated herein by reference, (4.79 g, 10 mmol) in anhydrous tetrahydrofuran (25 ml) was added benzylamine (6.42 g, 60 mmol). The mixture was stirred at room temperature overnight. The crude mixture was diluted with ethyl acetate (150 ml), washed with 0.1N aqueous hydrochloric acid (3×50 ml), water (50 ml) and brine (50 ml). The organic layer was dried over anhydrous magnesium sulphate.

After filtration and removal of the solvent in vacuo the residue was purified by flash chromatography.(silica gel, ethyl acetate/cyclohexane: 2:8) to give the title compound (3.80 g, 71% yield). Rf: 0.47 (ethyl acetate/cyclohexane) mp: 142° C. MS: [MH]⁺=541 [MNH₄]⁺=558 Analysis: for $C_{30}H_{34}N_2O_5F_2$, Calculated: C, 66.65; H, 6.34; N, 5.18 Found: C, 66.96; H, 6.34; N, 5.15.
STEP B:
4-Amino-2,2-Difluoro-3-Hydroxy-5[(4-Benzyloxy)Phenyl]N-Benzyl Pentanamide A solution of 4-tert-butoxycarbonylamino-2,2-difluoro-3-hydroxy-5[(4-benzyloxy)phenyl]N-benzyl pentanamide (0.65 g, 1.2 mmol) in formic acid (20 ml) was stirred at room temperature for 4 hours. The solvent was removed in vacuo. The residue was dissolved in ethyl acetate (60 ml) and washed with a saturated solution of sodium carbonate (3×10 ml), and brine (10 ml). The organic layer was dried over magnesium sulphate.

Filtration and removal of the solvent in vacuo yielded the title compound as a white solid (0.42 g, 80% yield) used without further purification in the next step. Rf: 0.62 (AcOH/nBuOH/H₂O: 2:6:2 MS: [MH]⁺=441 Analysis: for $C_{25}H_{26}N_2O_3F_2$, Calculated: C, 68.17; H, 5.95; N, 6.36 Found: C, 67.88; H, 5.88; N, 6.56.
STEP C:
4(N-Tert-Butoxycarbonyl-L-Valyl)Amino-2,2-Difluoro-3-Hydroxy-5[(4-Benzyloxy)Phenyl]N-Benzyl Pentanamide To a solution of N-tert-butoxycarbonyl-L-valyl-anhydride (0.387 g, 0.93 mmol) in anhydrous dichloromethane (10 ml) at room temperature, was added a solution of 4-amino-2,2-difluoro-3-hydroxy-5[(4-benzyloxy)phenyl]N-benzyl pentanamide (0.41 g, 0.93 mmol) in anhydrous N,N-dimethylformamide (3 ml) and anhydrous dichloromethane (2 ml). The mixture was stirred at room temperature overnight.

Evaporation and purification of the residue by flash chromatography (silica gel, gradient of ethyl acetate/cyclohexane: 2:8 to 1:1) afforded a white solid (0.45 g, 76% yield). Rf: 0.38 (AcOEt/cyclohexane: 1:1) MS: [MH]⁺=640 Analysis: for $C_{35}H_{43}N_3O_6F_2$, Calculated: C, 65.71; H, 6.77; N, 6.57 Found: C, 65.92; H, 6.87; N, 6.45.
STEP D:
4(N-Tert-Butoxycarbonyl-L-Valyl)Amino-2,2-Difluoro-3-Hydroxy-5[(4-(Hydroxy)Phenyl]N-Benzyl Pentanamide To a solution of 4(N-tert-butoxycarbonyl-L-valyl)amino-2,2-difluoro-3-hydroxy-5[(4-benzyloxy)phenyl]N-benzyl pentanamide (0.35 g, 0.55 mmol) in absolute ethanol (15 ml) and anhydrous N,N-dimethylformamide (5 ml) was added 10% Palladium in activated charcoal (0.1 g). This mixture was stirred at room temperature under atmospheric pressure of hydrogen overnight.

Filtration of the catalyst and evaporation in vacuo yielded 90% of the title compound (0.27 g) as a white solid. Rf: 0.29 (ethyl acetate/cyclohexane: 1:1).
STEP E:
4(N-Tert-Butoxycarbonyl-L-Valyl)Amino-2,2-Difluoro-3-Hydroxy-5[4(2-{N-Morpholinyl}Ethyloxy)Phenyl]N-Benzyl Pentanamide To a solution of 4(N-tert-butoxycarbonyl-L-valyl)amino-2,2-difluoro-3-hydroxyl-5[4(hydroxy)phenyl]N-benzyl pentanamide (0.27 g, 0.49 mmol) in anhydrous dioxane (20 ml) was added anhydrous cesium carbonate (0.422 g, 1.3 mmol), potassium iodide (0.01 g) and N-(2-chloroethyl) morpholine hydrochloride (0.111 g, 0.6 mmol). This mixture was heated under reflux for 72 hours. The crude mixture was diluted with ethyl acetate (100 ml) and washed three times with water and brine. The organic layer was dried over magnesium sulphate.

Filtration and evaporation of the solvent in vacuo afforded a residue which was purified by flash chromatography (silica gel, ethyl acetate). The title compound was obtained with 62% yield (0.2 g). Rf: 0.33 (CHCl$_3$/CH$_3$OH: 92:8) MS: [MH]$^+$=663.

STEP F:

4(L-Valyl)Amino-2,2-Difluoro-3-Hydroxy-5[4(2-{N-Morpholinyl}Ethyloxy)Phenyl]N-Benzyl Pentanamide A solution of 4(N-tert-butoxycarbonyl-L-valyl)amino-2,2-difluoro-3-hydroxy-5[4(2-{N-Morpholinyl}Ethyloxy)Phenyl]N-benzyl pentanamide (0.19 g, 0.28 mmol) in formic acid (15 ml) was stirred at room temperature for 4 hours. After evaporation of the solvent in vacuo, the residue was diluted with ethyl acetate (50 ml) and washed three times with a saturated solution of sodium carbonate (3×10 ml) and brine (10 ml). The organic layer was dried over magnesium sulphate.

Filtration and removal of the solvent in vacuo yielded the title compound as a white solid used without purification in the next step (0.11 g, 69% yield).

STEP G:

4(N-Benzyloxycarbonyl-L-Valyl)Amino-2,2-Difluoro-3-Hydroxy-5[4(2-{N-Morpholinyl}Ethyloxy)Phenyl]N-Benzyl Pentanamide To a solution of 4(L-valyl)amino-2,2-difluoro-3-hydroxy-5[4(2-{N-Morpholinyl}Ethyloxy)Phenyl]N-benzyl pentanamide (0.1 g, 0.18 mmol) in anhydrous dichloromethane (10 ml) was added benzyldicarbonate (0.055 g, 0.19 mmol). The mixture was stirred at room temperature overnight.

Evaporation of the solvent in vacuo, purification of the residue by flash chromatography (silica gel, CH$_2$Cl$_2$/CH$_3$OH:99:1) and recrystallization (ethyl acetate/pentane) afforded the title compound as a white solid (0.075 g, 60% yield). Rf: 0.38 (chloroform/methanol: 92:8) MS: [MH]$^+$= 697 Analysis: for C$_{37}$H$_{46}$N$_4$O$_7$F$_2$, Calculated with 0.25 H$_2$O: C, 63.77; H, 6.68; N, 7.98 Found: C, 63.34; H, 6.64; N, 8.08.

STEP H:

4(N-Benzyloxycarbonyl-L-Valyl)Amino-2,2-Difluoro-3-Oxo-5[4(2-{N-Morpholinyl}Ethyloxy)Phenyl]N-Benzyl Pentanamide To a solution of oxalyl chloride (0.102 g, 0.8 mmol) in anhydrous dichloromethane (1 ml) at −60° C., was added under nitrogen, dimethyl sulfoxide (distilled over calcium hydride) (0.125 g, 1.6 mmol) in anhydrous dichloromethane (1 ml). After 10 minutes stirring a solution of 4(N-benzyloxycarbonyl-L-valyl)amino-2,2-difluoro-3-hydroxy-5[4(2-{N-Morpholinyl}Ethyloxy)Phenyl]N-benzyl pentanamide (0.06 g, 0.08 mmol) in anhydrous dichloromethane (3 ml) was added. The mixture was stirred at −60° C. for 3 hours and the temperature was then allowed to rise to −10° C. Triethylamine (0.101 g, 1 mmol) in anhydrous dichloromethane (1 ml) was then added. The mixture was stirred for 15 hours while the temperature was allowed to rise to room temperature. The crude mixture was taken off in ethyl acetate (30 ml) and washed with 0.1N aqueous hydrochloric acid (3×8 ml), brine (8 ml) and dried over magnesium sulphate.

Filtration and removal of the solvent in vacuo yielded a crude residue which was purified by flash chromatography (silica gel, chloroform/methanol: 99:1). The title compound was isolated as a white solid (0.036 g, 61% yield). Rf: 0.40 (chloroform/methanol: 92:8) MS: [MH]$^+$=695 Analysis: for C$_{37}$H$_{44}$N$_4$O$_7$F$_2$, Calculated: C, 63.96; H, 6.38; N, 8.06 Found: C, 64.10; H, 6.50; N, 7.65 $^{19}$F NMR: shows mixture of two stereoisomers (40/60) and ketone/hydrate: 75/25.

EXAMPLE 2

4-(N-Benzyloxycarbonyl-L-Valyl)Amino-2,2-Difluoro-3-Oxo-5[4({2-Pyridyl}methyloxy)phenyl] N-Benzyl Pentanamide

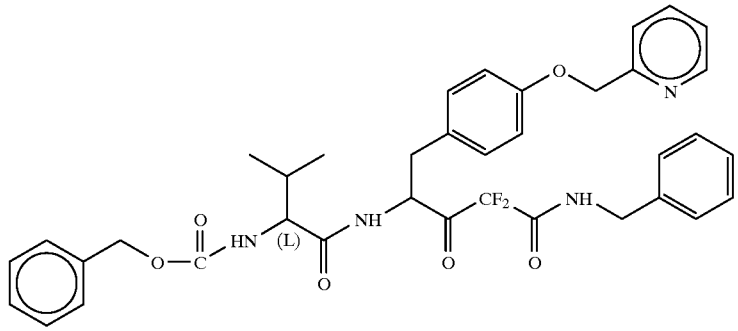

STEP A:

4-Tert-Butoxycarbonylamino-2, 2-Difluoro-3-Hydroxy-5 [(4-Hydroxy)Phenyl]N-Benzyl Pentanamide A solution of 4-(tert-butoxycarbonylamino-2,2-difluoro-3-hydroxy-5-[(4-benzyloxy)phenyl]N-benzyl-pentanamide (1.90 g, 3.5 mmol) in absolute ethanol (100 ml) was stirred with 10% Palladium on charcoal (0.6 g) at room temperature under atmospheric pressure of hydrogen overnight.

Filtration of the catalyst and evaporation in vacuo of the filtrate, yielded 89% of the title compound (1.40 g) as a white solid. Rf: 0.38 (ethyl acetate/cyclohexane) Analysis: for C$_{23}$H$_{28}$N$_2$O$_5$F$_2$, 0.25 H$_2$O: Calculated: C, 60.72; H, 6.31; N, 6.16 Found: C, 60.60; H, 6.25; N, 6.03.

STEP B:

4-Tert-Butoxycarbonylamino-2,2-Difluoro-3-Hydroxy-5 [4({2-pyridyl}methyloxy)phenyl]N-Benzyl Pentanamide To a solution of 4-tert-butoxycarbonylamino-2,2-difluoro-3-hydroxy-5[(4-hydroxy)phenyl]N-benzyl pentanamide (0.59 g, 1.3 mmol) in anhydrous dioxane (25 ml) was added anhydrous cesium carbonate (1.11 g, 3.4 mmol), potassium iodide (0.01 g) and 2-picolylchloride hydrochloride (0.246 g, 1.5 mmol). This mixture was heated under reflux for 6 hours. The crude mixture was diluted with ethyl acetate (150 ml) and washed three times with water and once with brine. The organic layer was dried over magnesium sulphate.

Filtration and evaporation in vacuo of the solvent afforded a residue which was purified by flash chromatography (silica gel, gradient of ethylacetate/cyclohexane: 3:7 to 1:1). The title compound was isolated with 40% yield (0.23 g). Rf: 0.49 (AcOEt/cyclohexane: 1:1) MS: [MH]$^+$=542.

STEP C:

4-Amino-2,2-Difluoro-3-Hydroxy-5[4({2-pyridyl}methyloxy)phenyl]N-Benzyl Pentanamide A solution of 4-tert-butoxycarbonylamino-2,2-difluoro-3-hydroxy-5[4({2-pyridyl}methyloxy)phenyl]N-benzyl pentanamide (0.28 g, 0.52 mmol) in formic acid (25 ml) was stirred at room temperature for 4 hours. The solvent was removed in vacuo. The residue was dissolved with ethyl acetate (60 ml) and washed with a saturated solution of sodium carbonate (3×20 ml) and brine, then dried over magnesium sulphate.

Filtration and removal of the solvent in vacuo yielded the title compound as a white solid (0.17 g, 75% yield) used without purification in the next step.

STEP D:

4-(N-Benzyloxycarbonyl-L-Valyl)Amino-2,2-Difluoro-3-Hydroxy-5[4({2-pyridyl}methyloxy)phenyl]N-Benzyl Pentanamide To a solution of Cbz-L-valyl-anhydride (0.184 g, 0.38 mmol) in anhydrous dichloromethane (8 ml) was added 4-amino-2,2-difluoro-3-hydroxy-5[4({2-pyridyl}methyloxy)phenyl]N-benzyl pentanamide (0.17 g, 0.38 mmol) in anhydrous dichloromethane (3 ml) and anhydrous N—N dimethylformamide (1 ml). This mixture was stirred at room temperature overnight.

The solvent was removed in vacuo and the residue purified by flash chromatography (silica gel, gradient of ethyl acetate/cyclohexane: 3:7 to 75:25). The title compound was isolated as a white solid (0.195 g, 76% yield). Rf: 0.45 (ethyl acetate) MS: [MH]$^+$=675 Analysis: for $C_{37}H_{40}N_4O_6F_2$, Calculated: C, 64.15; H, 6.11; N, 8.09 Found: C, 64.31; H, 6.05; N, 7.96 $^{19}$F NMR: shows mixture of 2 diastereoisomers 85/15.

STEP E:

4-(N-Benzyloxycarbonyl-L-Valyl)Amino-2,2-Difluoro-3-Oxo-5[4({2-pyridyl}methyloxy)phenyl]N-Benzyl Pentanamide To a solution of oxalyl chloride (0.303 g, 2.5 mmol) in anhydrous dichloromethane (3 ml) at −60° C. under nitrogen, was added a solution of dimethylsulfoxide (0.39 g, 5 mmol) in anhydrous dichloromethane (1 ml). After stirring for 10 minutes, a solution of 4-(N-benzyloxycarbonyl-L-valyl)amino-2,2-difluoro-3-hydroxy-5[4({2-pyridyl}methyloxy)phenyl]N-benzyl pentanamide (0.17 g, 0.25 mmol) in anhydrous dichloromethane (4 ml) was added. The mixture was stirred at −60° C. under nitrogen for 3 hours and the temperature was then allowed to rise to −10° C. Triethylamine (0.303 g, 3 mmol) in anhydrous dichloromethane (1 ml) was then added. The mixture was stirred for 15 hours while the temperature was allowed to rise to room temperature. The crude mixture was taken off in ethyl acetate (50 ml) and washed with 0.1N aqueous hydrochloric acid (3×10 ml). The organic layer was washed with water, brine and dried over magnesium sulphate.

After filtration and removal of the solvent in vacuo the residue was purified by flash chromatography (silica gel, gradient of ethyl acetate/cyclohexane: 4:6 to 75:25). The title compound was isolated as a white solid (0.09 g, 53% yield). Rf: 0.50 (AcOEt) MS: [MH]$^+$=673 Analysis: for $C_{37}H_{38}N_4O_6F_2$, Calculated: C, 66.06; H, 5.69; N, 8.33 Found: C, 66.12; H, 5.77; N, 8.15 $^{19}$F NMR: shows mixture of 2 stereoisomers 40/60.

EXAMPLE 3

4-(N-Benzyloxycarbonyl-L-Valyl)Amino-2,2-Difluoro-3-Oxo-5-[4-(4-Pentenyloxy)Phenyl]N-Benzyl Pentanamide

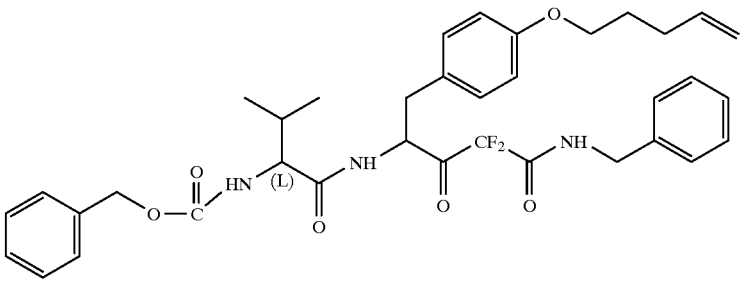

STEP A:

4-Tert-Butoxycarbonylamino-2,2-Difluoro-3-Hydroxy-5[4-(4-Pentenyloxy)Phenyl]N-Benzyl Pentanamide To a solution of the compound described in Example 2, Step A (0.45 g, 1 mmol) in anhydrous dioxane (15 ml) was added anhydrous potassium carbonate (0.116 g, 1.2 mmol), potassium iodide (0.01 g) and 5-bromo-1-pentene (1.64 g, 11 mmol). The mixture was heated under reflux for 3 days.

The crude mixture was diluted with ethyl acetate (100 ml) and washed three times with water and once with brine. The organic layer was dried over magnesium sulphate.

Filtration and evaporation in vacuo of the solvent afforded a residue, which was purified by flash chromatography (silica gel, gradient of ethyl acetate/cyclohexane 1:9 to 2:8). The title compound was isolated as a white solid with 31% yield (0.16 g). Rf: 0.53 (AcOEt/cyclohexane: 1:1) MS: [MH]$^+$=519 [MNH$_4$]$^+$=536.

STEP B:

4-Amino-2,2-Difluoro-3-Hydroxy-5[4-(4-Pentenyloxy) Phenyl]N-Benzyl Pentanamide

A solution of 4-tert-butoxycarbonylamino-2,2-difluoro-3-hydroxy-5[4-(4-pentenyloxy)phenyl]N-benzyl pentanamide (0.16 g, 0.30 mmol) in formic acid (10 ml) was stirred at room temperature for 4 hours. The solvent was removed in vacuo.

The residue was dissolved in ethyl acetate (60 ml) and washed three times with a saturated solution of sodium carbonate (3×20 ml) and brine (20 ml), then dried over anhydrous magnesium sulphate.

Filtration and removal of the solvent in vacuo yielded the title compound as a white solid (0.08 g, 63% yield) used without purification in the next step.

STEP C:

4-(N-Benzyloxycarbonyl-L-Valyl)Amino-2,2-Difluoro-3-Hydroxy-5-[4-(4-Pentenyloxy)Phenyl]N-Benzyl Pentanamide To a solution of Cbz-L-Valyl anhydride (0.092 g, 0.20 mmol) in anhydrous dichloromethane (10 ml) was added 4-amino-2,2-difluoro-3-hydroxy-5[4-(oxo-4-pentenyl)phenyl]N-benzyl pentanamide (0.08 g, 0.19 mmol) in anhydrous dichloromethane (3 ml). The mixture was stirred at room temperature overnight.

The solvent was removed in vacuo and the residue purified by flash chromatography (silica gel, ethyl acetate/cyclohexane: 3:7).

The title compound was isolated as a white solid (0.09 g, 73% yield). Rf: 0.37 (ethyl acetate/cyclohexane: 1:1) MS: [MH]$^+$=652.

STEP D:

4-(N-Benzyloxycarbonyl-L-Valyl)Amino-2,2-Difluoro-3-Oxo-5[4-(4-Pentenyloxy)Phenyl]N-Benzyl Pentanamide To a solution of oxalyl chloride (0.178 g, 1.4 mmol) in anhydrous dichloromethane (10 ml) at −60° C. under nitrogen was added a solution of anhydrous dimethyl sulfoxide (0.218 g, 2.8 mmol) in anhydrous dichloromethane (1 ml). After 10 minutes stirring a solution of 4-(N-benzyloxycarbonyl-L-valyl)amino-2,2-difluoro-3-hydroxy-5[4-oxo-(4-pentenyloxy)phenyl]N-benzyl pentanamide (0.09 g, 0.14 mmol) in anhydrous dichloromethane (3 ml) was added.

The mixture was stirred at −60° C. under nitrogen for 3 hours and the temperature was then allowed to rise to −10° C. Triethylamine (0.162 g, 1.6 mmol) in anhydrous dichloromethane (1 ml) was then added. The mixture was stirred for 15 hours while the temperature was allowed to rise to room temperature.

The crude mixture was taken off in ethylacetate (50 ml) and washed with 0.1N aqueous hydrochloric acid (3×10 ml). The organic layer was washed with water, brine and dried over anhydrous magnesium sulphate.

After filtration and removal of the solvent in vacuo, the residue was purified by flash chromatography (silica gel, ethyl acetate/cyclohexane 2:8).

The title compound was obtained as a white solid (0.038 g, 43% yield). Rf: 0.39 (ethyl acetate/cyclohexane: 1:1) MS: [MH]$^+$=650 [MNH$_4$]$^+$=667 Analysis: for $C_{36}H_{41}N_3O_6F_2$, Calculated: C, 66.55; H, 6.36; N, 6.47 Found: C, 65.75; H, 6.09; N, 5.79 $^{19}$F NMR: shows mixture of 2 stereoisomers 65/35 and ketone/hydrate 83/17.

EXAMPLE 4

N[3-(3-Pyridyl)Propanoyl]4-(L-Valyl)Amino-2,2-Difluoro-3-Oxo-5[4-2{N-morpholinyl}ethyloxy)phenyl]N-Benzyl Pentanamide

STEP A:

N[3-(3-Pyridyl)Propanoyl]4-(L-Valyl)Amino-2,2-Difluoro-3-Hydroxy-5[4(2-{N-Morpholinyl}Ethyloxy)Phenyl]N-Benzyl Pentanamide To a solution of N-[3-(3-pyridyl)propanoyl]4-(L-valyl)amino-2,2-difluoro-3-hydroxy-5[(4-hydroxy)phenyl]N-benzyl pentanamide (0.17 g, 0.29 mmol) in anhydrous dioxane (20 ml) was added anhydrous cesium carbonate (0.325 g), 1 mmol) potassium iodide (0.01 g) and N-2-chloroethyl morpholine hydrochloride (0.075 g, 0.40 mmol). This mixture was heated under reflux overnight. The crude mixture was evaporated in vacuo and the residue was purified by flash chromatography (silica gel, gradient of dichloromethane:methyl alcool: 98:2 to 92:8).

The title compound was isolated as a white solid (75% yield, (0.15 g). Rf: 0.49 (dichloromethane/methyl alcohol: 9:1) MS: [MH]$^+$=696

STEP B:

N[3-(3-Pyridyl)Propanoyl]4-(L-Valyl)Amino-2,2-Difluoro-3-Oxo-5[4(2-{N-Morpholinyl}Ethyloxy)Phenyl]N-Benzyl Pentanamide To a solution of oxalyl chloride (0.254 g, 2 mmol) in anhydrous dichloromethane under nitrogen at −60° C., was added a solution of dimethyl sulfoxide (0.312 g, 4 mmol) in anhydrous dichloromethane (2 ml). After 10 minutes stirring at −60° C., a solution of N[3-(3-pyridyl)propanoyl]4-(L-valyl)amino-2,2-difluoro-3-hydroxy-5[4(2-{N-morpholyl}ethyloxy)phenyl]N-benzyl pentanamide (0.14 g, 0.20 mmol) in anhydrous dichloromethane (5 ml) was added.

The mixture was stirred at −60° C. under nitrogen for 4 hours and then the temperature was allowed to rise to −10° C. Triethylamine (0.303 g, 3 mmol) in anhydrous dichloromethane (1 ml) was then added and the mixture was stirred under nitrogen for 15 hours, while the temperature was allowed to rise to room temperature. The crude mixture was taken off in ethylacetate (50 ml) and washed with water (3×10 ml) and brine (10 ml) then dried over anhydrous magnesium sulphate.

Filtration and removal of the solvent in vacuo a residue which was purified by flash chromatography (silica gel, gradient of dichloromethane/methanol: 98:2 to 92:8). The title compound was isolated as a pale yellow solid (10% yield, 0.014 g). Rf: 0.51 (dichloromethane/methanol: 9:1) MS: [MH]$^+$=694

EXAMPLE 5

N[3-(3-Pyridyl)Propanoyl]4-(L-Valyl)Amino-2,2-Difluoro-3-Oxo-5[4({2-pyridyl}methyloxy)phenyl]N-Benzyl Pentanamide

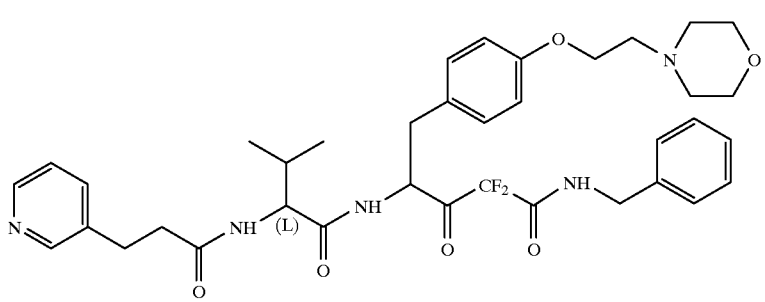

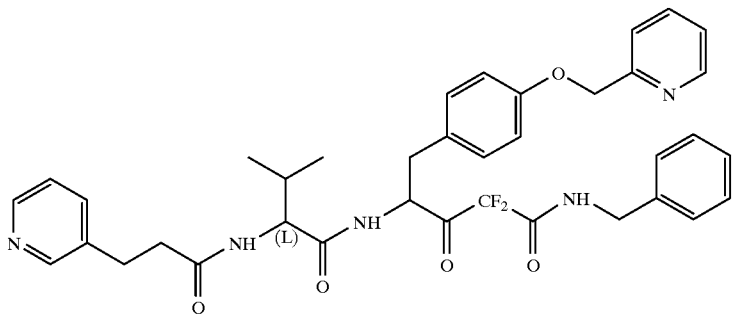

STEP A:

4-(L-Valyl)Amino-2,2-Difluoro-3-Hydroxy-5[(4-(Benzyloxy)Phenyl]N-Benzyl Pentanamide A solution of 4(N-tert-butoxycarbonyl-L-valyl)amino-3,3-difluoro-3-hydroxy-5[(4-benzyloxy)phenyl]N-benzyl pentanamide (1.28 g, 2 mmol) in formic acid (50 ml) was stirred at room temperature for 4 hours. The solvent was removed in vacuo and the residue was dissolved in ethyl acetate (100 ml) and washed three times with a saturated solution of sodium carbonate (3×30 ml), once with brine (30 ml). The organic layer was dried over anhydrous magnesium sulphate.

Filtration and removal of the solvent in vacuo yielded the title compound as a white solid (0.90 g, 84% yield), used without purification in the next step.

STEP B:

N[3-(3-Pyridyl)Propanoyl]4-(L-Valyl)Amino-2,2-Difluoro-3-Hydroxy-5[(4-Benzyloxy)Phenyl]N-Benzyl Pentanamide To a solution of 3-(3-pyridyl)propionic acid (0.242 g, 1.6 mmol) in anhydrous acetonitrile (10 ml) was added N-methyl morpholine (0.182 g, 1.8 mmol) in anhydrous acetonitrile (1 ml). The mixture under nitrogen was cooled to −20° C. and isobutylchloroformate (0.218 g, 1.6 mmol) in anhydrous acetonitrile (2 ml) was added. After 10 minutes stirring at −20° C. under nitrogen, 4-(L-valyl)amino-2,2-difluoro-3-hydroxy-5[(4-benzyloxy)phenyl]N-benzyl pentanamide (0.9 g, 1.6 mmol) in anhydrous N,N-dimethyl formamide (10 ml) was added.

The mixture was stirred at −20° C. under nitrogen for 4 hours and then the temperature was allowed to rise to room temperature overnight. The crude mixture was evaporated in vacuo and the residue was purified by flash chromatography (silica gel, gradient of dichloromethane/methyl alcohol: 99:1 to 92:8). The title compound was obtained as a white solid (0.8 g, 75% yield). Rf: 0.36 (dichloromethane/methanol: 92:8) MS: [MH]$^+$=673 Analysis: for $C_{36}H_{42}N_4O_5F_2$, Calculated: C, 66.95; H, 6.36; N, 8.22 Found: C, 66.71; H, 6.19; N, 8.04

STEP C:

N[3-(3-Pyridyl)Propanoyl]4-(L-Valyl)Amino-2,2-Difluoro-3-Hydroxy-5[(4-Hydroxy)Phenyl]N-Benzyl Pentanamide A solution of N[3-(3-pyridyl)propanoyl]4-(L-valyl)amino-2,2-difluoro-3-hydroxy-5[(4-benzyloxy)phenyl]N-benzyl pentanamide (0.43 g, 0.64 mmol) in absolute ethanol (20 ml) and N,N-dimethylformamide (5 ml) was stirred with 10% palladium on charcoal (0.12 g) at room temperature under atmospheric pressure of hydrogen overnight.

Filtration of the catalyst and evaporation in vacuo of the filtrate, yielded 81% the title compound (0.3 g) as a white solid. Rf: 0.20 (dichloromethane/methanol: 92:8) MS: [MH]$^+$=582

STEP D:

[3-(3-Pyridyl)Propanoyl]4-(L-Valyl)Amino-2,2-Difluoro-3-Hydroxy-5[4({2-pyridyl}methyloxy)phenyl]N-Benzyl Pentanamide To a solution of N[3-(3-pyridyl)propanoyl]4-(L-valyl)amino-2,2-difluoro-3-hydroxy-5[(4-(hydroxy)phenyl]N-benzyl pentanamide (0.3 g, 0.51 mmol) in anhydrous dioxane (50 ml) was added anhydrous cesium carbonate (0.43 g, 1.3 mmol) potassium iodide (10 mg) and 2-picolyl chloride (0.108 g, 0.66 mmol). This mixture was heated under reflux for 30 hours. The crude mixture was diluted with ethyl acetate (100 ml) and washed three times with water (3×20 ml) and once with brine. The organic layer was dried over anhydrous magnesium sulphate.

Filtration and evaporation in vacuo of the solvent afforded a residue which was purified by flash chromatography (silica gel, gradient of dichloromethane/methyl alcohol: 98:2 to 92:8). The title compound was isolated as a white solid (41% yield, 0.140 g). Rf: 0.47 (dichloromethane/methanol: 9:1) MS: [MH]$^+$=674 Analysis: for $C_{37}H_{41}N_5O_5F_2$, Calculated: C, 65.96; H, 6.13; N, 10.39 Found: C, 64.13; H, 5.87; N, 10.11 $^{19}$F NMR: shows mixture of stereoisomers 80/20.

STEP E:

N[3-(3-Pyridyl)Propanoyl]4-(L-Valyl)Amino-2,2-Difluoro-3-Oxo-5[4({2-pyridyl}methyloxy)phenyl]N-Benzyl Pentanamide To a solution of oxalyl chloride (0.085 g, 0.67 ml) in anhydrous dichloromethane (5 ml) under nitrogen at −60° C., was added a solution of dimethylsulfoxide (0.11 g, 0.70 mmol) in anhydrous dichloromethane (2 ml). After 10 minutes stirring at −60° C., a solution of N[3-(3-pyridyl)propanoyl]4-(L-valyl)amino-2,2-difluoro-3-hydroxy-5[4({2-pyridyl}methyloxy)phenyl]N-benzyl pentanamide (0.045 g, 0.067 mmol) in anhydrous dichloromethane (3 ml) was added. The mixture was stirred at −60° C. under nitrogen for 4 hours and then the temperature was allowed to rise to −10° C. Triethylamine (0.202 g, 2 mmol) in anhydrous dichloromethane (2 ml) was then added, and the mixture was stirred for 15 hours, while the temperature was allowed to rise to room temperature. The crude mixture was taken off in ethyl acetate (50 ml) and washed with 0.1N aqueous hydrochloric acid (3×10 ml). The organic layer was washed with water brine and dried over magnesium sulphate.

After filtration and removal of the solvent in vacuo the residue was purified by flash chromatography (silica gel, gradient of dichloromethane/methyl alcohol): 98:2 to 95:5). The title compound was isolated as a white solid 44% yield, 0.019 g). Rf: 0.50 (dichloromethane/methanol: 9:1) MS: [MH]$^+$=672

EXAMPLE 6

N-[4-(N-Benzyloxycarbonyl-L-valyl)amino-2,2-difluoro-1,3-dioxo-5-(4-{2-N-morpholinyl}ethyloxy)phenyl-pentyl]-O-benzyl-D-valinol

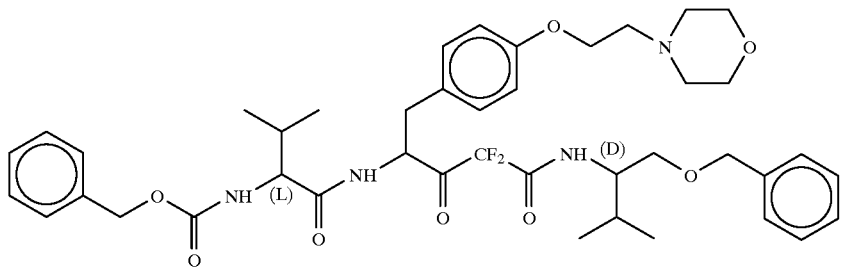

STEP A:
4-Tert-Butoxycarbonylamino-2,2-Difluoro-3-Hydroxy-5-(4-Hydroxy)Phenyl Pentanoic Acid, Ethyl Ester A solution of 4-tert-butoxycarbonylamino-2,2-difluoro-3-hydroxy-5-[(4-benzyloxy)phenyl]N-benzyl pentanamide (0.719 g, 1.5 mmol) in ethanol (50 ml) was kept for 7.5 hours under an hydrogen atmosphere in the presence of 10% palladium on charcoal (0.074 g). The hydrogen atmosphere was exchanged by a nitrogen atmosphere, the suspension was filtered off and the solution concentrated in vacuo. The title derivative thus obtained was used as such in the next step (0.500 g, 83% yield). Rf: 0.51 (silica gel, petroleum ether/ethyl acetate: 1/1).

STEP B:
N-Tert-Butoxycarbonyl-D-Valinol

A solution of D-valinol (5.1 g, 49.4 mmol) and di-tert-butyldicarbonate (10.9 g, 52 mmol) in methanol (60 ml) was stirred for 17 hours at room temperature. After concentration in vacuo, the residue was purified by flash chromatography (silica gel, ethyl acetate/petroleum ether: 3/7, Rf: 0.37) to give the title compound in quantitative yield (10.07 g, colorless oil). MS: MH$^+$=204.

STEP C;
N-Tert-Butoxycarbonyl-O-Benzyl-D-Valinol

To a solution of N-tert-butoxycarbonyl-D-valinol (10 g, 49.3 mmol) and benzylbromide (5.86 ml, 49.3 mmol) in anhydrous dimethyl formamide (50 ml) was added at −5° C. and under nitrogen, potassium-tert-butoxide (11.06 g, 98.6 mmol) as a solid, portionwise, an in such a way that the internal temperature does not exceed +5° C. The reaction mixture was stirred for 2 hours at 0° C., diluted with ethyl acetate (2×300 ml), extracted with a 1N solution of potassium hydrogenosulfate (50 ml) and water (250 ml) and washed twice with water (2×200 ml). After drying of the organic phase on sodium sulfate, filtration and concentration in vacuo, the resulting oil was purified by flash chromatography (silica gel, ethyl acetate/petroleum ether: 1/9, Rf: 0.42) to give the title compound as a colorless oil (9.95 g, 69% yield). MS: [MH]$^+$=294.

STEP D:
O-Benzyl-D-Valinol

A solution of N-tert-butoxycarbonyl-O-benzyl-D-valinol (9.95 g, 34 mmol) in formic acid (50 ml) was stirred for 4 hours at room temperature. After removal of the formic acid in vacuo, the sticky residue was dissolved in water (100 ml), neutralized with a saturated solution of sodium bicarbonate (100 ml) and the organic material extracted twice with ethyl acetate (2×200 ml). The organic phases were washed until neutral with water (2×200 ml) and the combined organic layers were dried on sodium sulfate. Filtration and evaporation of the solvent in vacuo afforded the title amine as a slightly yellowish oil (5.20 g, 79%). MS: [MH]$^+$=194.

STEP E:
N-[4-Tert-Butoxycarbonylamino-2,2-Difluoro-3-Hydroxy-1-Oxo-5-(4-Hydroxy)Phenyl-Pentyl]O-Benzyl-D-Valinol The title compound is obtained from the compounds described in Example 6, Steps A and D, following the method given in Example 1, Step A.

STEP F:
N-[4-Tert-Butoxycarbonylamino-2,2-Difluoro-3-Hydroxy-1-Oxo-5-(4-{2-N-Morpholinyl}Ethyloxy)Phenyl-Pentyl]O-Benzyl-D-Valinol The title derivative is obtained from the phenol of Example 6, Step E and N-(2-chloroethyl)morpholine, hydrochloride using the procedure of Example 1, Step E.

STEP G:
N-[4-Amino-2,2-Difluoro-3-Hydroxy-1-Oxo-5-(4-{2-N-Morpholinyl}Ethyloxy)Phenyl-Pentyl]O-Benzyl-D-Valinol The title amine is prepared from the compound of Example 6, Step F using the deprotection procedure described in Example 1, Step B.

STEP H:
N-[4-(N-Butoxycarbonyl-L-Valyl)Amino-2,2-Difluoro-3-Hydroxy-1-Oxo-5-(4-{2-N-Morpholinyl}Ethyloxy) Phenyl-Pentyl]O-Benzyl-D-Valinol The title compound is obtained from the amine of Example 6, Step G and N-benzyloxycarbonyl-L-valyl anhydride following the procedure given in Example 1, Step C.

STEP I:
N-[4-(N-Benzyloxycarbonyl-L-Valyl)Amino-2,2-Difluoro-1,3-Dioxo-5-(4-{2-N-Morpholinyl}Ethyloxy) Phenyl-Pentyl]O-Benzyl Valinol The title derivative is obtained from the alcohol of Example 6, Step H using the oxidation method described in Example 1, Step H.

EXAMPLE 7

N-[4-(N-Benzyloxycarbonyl-L-Valyl)Amino-2,2-Difluoro-1,3-Dioxo-5-(4-{2-N-Morpholinyl}Ethyloxy)Phenyl-Pentyl]O-Methyl-D-Valinol

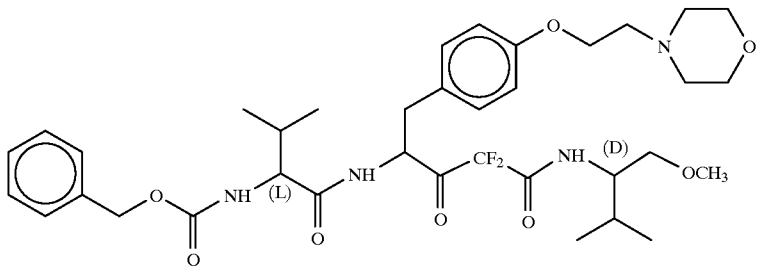

STEP A:

N-Tert-Butoxycarbonyl-O-Methyl-D-Valinol

The title compound has been prepared in 67% yield from the alcohol of Example 6, Step B and methyl iodide following the alkylation method given in Example 6, Step C. Rf: 0.27 (silica gel, ethyl acetate/petroleum ether: 1/9).

STEP B:

O-Methyl-D-Valinol

A solution of compound of Example 7, Step A (1.9 g, 8.76 mmol) in dry diethyl ether saturated with HCl gas was kept for 2 hours at room temperature. The solvent was removed in vacuo. The residue was dissolved in a minimum amount of a 95/5 mixture of dichloromethane and diethylamine and purified by flash chromatography on silica gel using the same mixture of solvents. The title amine was obtained in 59% yield. Rf: 0.01 (ethyl acetate/methanol: 8/2).

STEP C:

N-[4-Tert-Butoxycarbonylamino-2,2-Difluoro-3-Hydroxy-1-Oxo-5-(4-Hydroxy)Phenyl-Pentyl]O-Methyl-D-Valinol The title derivative is obtained from the compound of Example 6, Step A and the amine of Example 7, Step B following the reaction procedure given in Example 1, Step A (79% yield). Rf: 0.16 (ethylacetate/petroleum ether: 4:6) MS: $[MH]^+=461$.

STEP D

N-[4-Tert-Butoxycarbonylamino-2,2-Difluoro-3-Hydroxy-1-Oxo-5-(4-{2-N-Morpholinyl}Ethyloxy)Phenyl-Pentyl]O-Methyl-D-Valinol The title compound is prepared from the phenol of Example 7, Step C and N-(2-chloroethyl)morpholine, hydrochloride using the method described in Example 1, Step E (58% yield). Rf: 0.18 (ethylacetate).

STEP E:

N-[4-Amino-2,2-Difluoro-3-Hydroxy-1-Oxo-5-(4-{2-N-Morpholinyl}Ethyloxy)Phenyl-Pentyl]O-Methyl-D-Valinol The title amine is obtained from the compound of Example 7, Step D using the deprotection method given in Example 1, Step B (85% yield).

STEP F:

N-[4(N-Benzyloxycarbonyl-L-Valyl)Amino-2,2-Difluoro-3-Hydroxy-1-Oxo-5-(4-{2-N-Morpholinyl}Ethyloxy)Phenyl-Pentyl]O-Methyl-D-Valinol The title alcohol is obtained from the amine of Example 7, Step E and N-benzyloxycarbonyl-L-valyl anhydride using the coupling procedure given in Example 1, Step C (78% yield). Rf: 0.24 (dichloromethane/methanol: 95:5) MS: $[MH]^+=707$ Analysis: for $C_{36}H_{52}N_4O_8F_2$, 0.5 $H_2O$ Calculated: C, 60.40; H, 7.46; N, 7.83 Found: C, 60.29; H, 7.36; N, 7.78

STEP G:

N-[4(N-Benzyloxycarbonyl-L-Valyl)Amino-2,2-Difluoro-1,3-Dioxo-5-(4-{2-N-Morpholinyl}Ethyloxy) Phenyl-Pentyl]O-Methyl-D-Valinol A mixture of the alcohol of example 7, step F (0.130 g, 0.184 mmol), 1,1,1-tris(acetyloxy)-1,1-dihydro-1,2-benziodoxol-3(1H)-one (Dess Martin periodane, 0.312 g, 0.736 mmol) and tert-butanol (0.035 ml, 0.368 mmol) in freshly distilled dichloromethane (over phosphorus pentoxyde, 5 ml) is stirred for 15 minutes at room temperature. The reaction mixture is hydrolyzed with isopropanol (0.6 ml) and concentrated in vacuo. The residue is suspended in dichloromethane (1.5 ml), filtered through a Fluoropore filter which is rinsed twice with dichloromethane (2×1 ml) and the filtrate is concentrated in vacuo (0.335 g). Purification by flash chromatography (silica gel, dichloromethane/methanol: 98:2 to remove the byproducts coming from the Dess Martin reagent, then 96:4 to recover the title ketone (0.109 g) and impure ketone largely contaminated with the starting alcohol (0.121 g). These impure material has been oxidized a second time following the above procedure to give more ketone (0.099 g). The combined batches (0.208 g) are crystallized from ethylacetate/pentane to give the title ketone in 69% yield. Rf: 0.1 (dichloromethane/methanol: 95:5) MS: $[MH]^+=704$ Analysis: for $C_{36}H_{50}N_4O_8F_2$, 0.75 $H_2O$ Calculated: C, 60.20; H, 7.23; N, 7.80 Found: C, 60.28; H, 7.26; N, 7.94

The compounds of the present invention are useful as inhibitors of retroviral proteases required for replication, particularly the HIV-1 and HIV-2 viral proteases, the prevention or treatment of infection by the human immunodeficiency virus (HIV), and the treatment of consequent pathological conditions such as the acquired immunodeficiency syndrome (AIDS) in mammals capable of being infected with HIV virus. Treating AIDS, preventing infection by HIV or treating infection by HIV, is defined as including, but not limited to, treating a wide range of states of HIV infection: AIDS, ARC (AIDS related complex), both symptomatic and asymptomatic, and actual or potential exposure to HIV. For example, the compounds of this invention are useful in preventing infection by HIV after suspected past exposure to HIV by, e.g., blood transfusion, accidental needle stick, or exposure to patient blood during surgery.

The term "stereoisomers" is a general term for all isomers of individuals molecules that differ only in the orientation of their atoms in space. It includes mirror image isomers (enantiomers), geometric (cis/trans) isomers, and isomers of compounds with more than one chiral center that are not mirror images of one another (diastereoisomers). For aminoacids, the designations L/D, or R/S can be used as described in IUPAC-IUB Joint Commission on Biochemichal Nomenclature, Eur. J. Biochem. 138: 9–37 (1984).

For these purposes, the compounds of the present invention may be administered orally, parenterally (including subcutaneous injections, intravenous, intramuscular, transdermal, intrasternal injection or infusion techniques), by inhalation spray, or rectally, in dosage unit formulations containing convention non-toxic pharmaceutically acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; steriel injectable preparations, for example, as sterile injectable aqueous or oleagenous suspensions or suppositories) or they may be administered transdermally.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetener/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidize and/or dissolve in the rectal cavity to release the drug.

Dosage levels of the order of 0.02 to 5.0 or 10.0 grams per day are useful in the treatment or prevention of the above-indicated conditions, with oral doses being higher. For example, infection by HIV is effectively treated by the administration of from 1 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination the severity of the particular condition, and the host undergoing therapy. Preferred compounds are when $P_2$ is $C_{1-6}$ alkyl and especially $C_{1-3}$ alkyl, W and/or W' are $C_{1-3}$ alkyl, and/or R and/or R' are morpholinyl, $C_{1-4}$ alkylenyl or piperidyl.

The present invention is also directed to combinations of the HIV protease-inhibitory compounds with one or more agents useful in the treatment of AIDS, such as, for example, with known antiviral agents suitable for treating HIV 1 and HIV 2 viral infections, e.g., AZT, with or without a PNPase inhibitor, or in conjunctive therapy with DDI and a PNPase inhibitor.

The compounds of this invention may be assayed for their HIV-protease inhibition using the following published techniques.

Preparation of Retroviral Enzyme and Assay for Inhibition of the Protease

A) Preparation of Retroviral Enzyme

To prepare the recombinant protease, the HIV protease was expressed via *E. Coli* by the published work of C. Guénet, et al., in European Journal of Pharmacology, Molecular Pharmacology Section, 172 (1989) 443–451.

B) Assay for Inhibition of Recombinant Viral Protease

Inhibition of the reaction of the protease with a peptide substrate [Ser-Gln-Asn-Tyr-Pro-Ile-Val-NH$_2$, Km=1 mM were in 50 mM Na acetate, 10% glycerol, 5% ethyleneglycol, pH 5.5, at 37° C. for 1 hour. Various concentrations of inhibitor in 10 $\mu$l DMSO were added to 80 $\mu$l of assay solution and the reaction initiated by the addition of 10 $\mu$l (1.6 $\mu$g) of recombinant protease. The reaction was quenched with 16 $\mu$l of 4M perchloric acid. Products of the reaction were separated by HPLC (VYDAC wide pore 5 cm C-18 reverse phase, acetonitrile gradient, 0.1% trifluoroacetic acid). The extent of inhibition of the reaction was determined from the peak heights of the products. HPLC of the products, independently synthesized, provided quantitation standards and confirmation of the product composition.

By following the techniques referenced above, as well as by utilization of other known techniques, as well as by comparison with compounds known to be useful for treatment of the above-mentioned disease states, it is believed that adequate material is available to enable one of ordinary skill in the art to practice the invention.

As is true for most classes of compounds found to be useful in the pharmaceutical industry, certain subgeneric groups and certain specific compounds are more preferred such as those exemplified and shown in the following charts.

| $R_1$ | $P_2$ | $P_1$ | $R_6$ = H, $R_5$ |
|---|---|---|---|
| benzyl | isopropyl | 4-[(3-pyridyl)methyloxy]benzyl | benzyl |
| 3-pyridylethyl | isopropyl | 4-pentenyl | 2-pyridylmethyl |
| benzyl | isopropyl | 4-[(2-pyridyl)methyloxy]benzyl | benzyl |
| benzyl | isopropyl | 4-[(2-pyridyl)methyloxy]benzyl | 2-pyridylmethyl |
| benzyl | isopropyl | 4-[(3-pyridyl)methyloxy]benzyl | 2-pyridylmethyl |
| (3-pyridyl)ethyl | isopropyl | 4-[(3-pyridyl)methyloxy]benzyl | benzyl |
| benzyl | t-butyl | 4-[(2-pyridyl)methyloxy]benzyl | 3-pyridylmethyl |

-continued

| $R_1$ | $P_2$ | $P_1$ | $R_6$ = H, $R_5$ |
|---|---|---|---|
| benzyl | t-butyl | 4-[(3-pyridyl)methyloxy]benzyl | $R_6, R_5 =$ 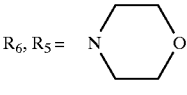 ] |
| (2-pyridyl)ethyl | isopropyl | 4-[(3-pyridyl)methyloxy]benzyl | $R_6, R_5 =$ 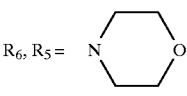 ] |
| 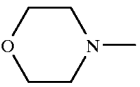 | phenyl | 4-[(3-pyridyl)methyloxy]benzyl | benzyl |
| benzyl | isopropyl | 4-[(4-pyridyl)methyloxy]benzyl | benzyl |
| benzyl | isopropyl | 4-[(2-pyridyl)methyloxy]benzyl | 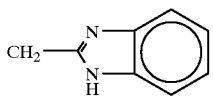 ] |
| (3-pyridyl)ethyl | isopropyl | 4-[(3-pyridyl)methyloxy]benzyl | benzyl |
| benzyl | isopropyl | 4-[2-(N-morpholyl)ethyloxy]benzyl | 3-pyridylmethyl |
| (2-pyridyl)ethyl | cyclopentyl | 4-[2-(N-morpholyl)ethyloxy]benzyl | benzyl |
| benzyl | isopropyl | 4-[2-(N-morpholyl)ethyloxy]benzyl | 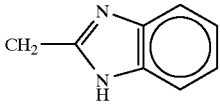 |
| benzyl | isopropyl | 4-[2-(N-morpholyl)ethyloxy]benzyl | 2-pyridylmethyl |
| benzyl | isopropyl | 4-[2-(N-morpholyl)ethyloxy]benzyl | 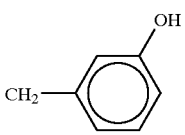 |
| benzyl | isopropyl | 4-[2-(N-morpholyl)ethyloxy]benzyl | 2-pyridylmethyl |
| benzyl | t-butyl | 4-[2-(N-morpholyl)ethyloxy]benzyl | 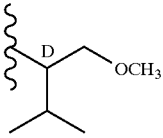 |
| benzyl | t-butyl | 4-[2-(N-morpholyl)ethyloxy]benzyl | 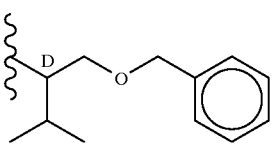 |

-continued

| $R_1$ | $P_2$ | $P_1$ | $R_6$ = H, $R_5$ |
|---|---|---|---|
| (3-pyridyl)ethyl | isopropyl | 4-[2-(pyridyl)methyloxy]benzyl | 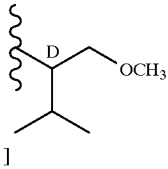 ] |
| (3-pyridyl)ethyl | isopropyl | 4-[3-(pyridyl)methyloxy]benzyl | 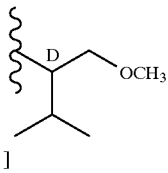 ] |
| (3-pyridyl)ethyl | t-butyl | 4-[4-(pyridyl)methyloxy]benzyl | 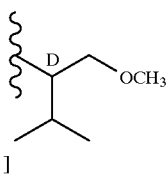 ] |
| benzyl | isopropyl | 4-[2-(pyridyl)methyloxy]benzyl | 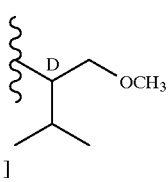 ] |
| (3-pyridyl)ethyl | isopropyl | 4-[2-(pyridyl)methyloxy]benzyl | 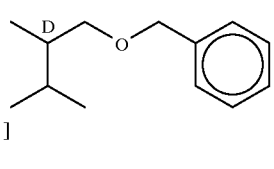 ] |
| benzyl | isopropyl | 4-[2-(N-morpholyl)ethyloxy]benzyl | 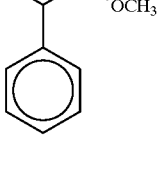 |
| (2-pyridyl)ethyl | isopropyl | 4-[3-(pyridyl)methyloxy]benzyl | 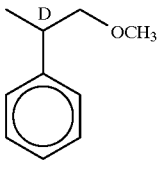 ] |
| benzyl | isopropyl | 4-[2-(N-piperidyl)ethyloxy]benzyl | 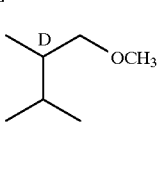 |
| (3-pyridyl)ethyl | isopropyl | 4-[(2-pyridyl)methyloxy)benzyl | 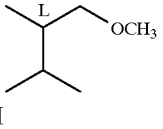 [ |

| R₁ | P₂ | P₁ | R₆ = H, R₅ |
|---|---|---|---|
| benzyl | isopropyl | 4-[(2-N-morpholyl)ethyloxy]benzyl | 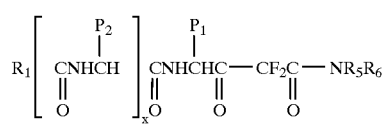 |
| benzyl | phenyl | 4-[(2-N-morpholyl)ethyloxy]benzyl | |
| (3-pyridyl)ethyl | isopropyl | 4-[(2-N-morpholyl)ethyloxy]benzyl | 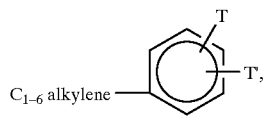 |

What is claimed is:

1. A compound of Formula 1

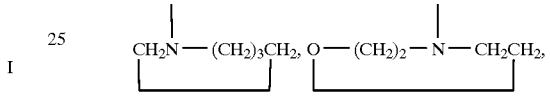

and the stereoisomers, hydrates, isosteres and the pharmaceutically acceptable salts thereof wherein $P_1$ is

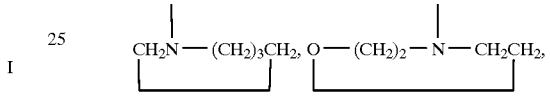

wherein

T is $[(O)_b\text{—}W\text{—}R]$ and T' is $[(O)_{b'}\text{—}W'\text{–}R']$ or H, wherein each of W and W' are independently $C_{1-6}$ alkylene or nothing, provided that W is $C_{2-6}$ alkylene when W is directly attached to a nitrogen atom in R, provided that W' is $C_{2-6}$ alkylene when W' is directly attached to a nitrogen atom in R';

$P_2$ is $C_{1-6}$ alkyl, cyclopentyl, hydroxy $C_{1-6}$ alkyl, phenyl, benzyl- or 3-tetrahydrofuryl;

R and R' are each independently $C_{2-6}$ alkenyl, piperazinyl, substituted piperazinyl, piperidyl, morpholinyl, pyridyl, pyrazinyl, or pyrimidinyl, wherein substituted piperazinyl is piperazinyl substituted on one nitrogen atom thereof with CHO, C(O)NHR₄, $C_{1-4}$ alkyl or $CO_2R_4$;

$R_1$ is benzyloxy, $C_{1-6}$ alkoxy, $C_{1-6}$ alkyl, phenyl, benzyl, phenethyl, fluorenylmethylenoxy, 2-quinolinyl, PDL,

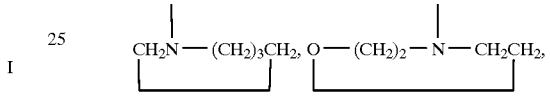

$NHSO_2R_4$, $N(R_4)(benzyl)$, or $N(R_4)(PDL)$;

PDL is $-(CH_2)_a\text{-}2\text{-},\ 3\text{-},$ or 4-pyridyl, or p-substituted benzyloxy, wherein the substitution is with a nitro, OH, amino, $C_{1-6}$ alkoxy, hydroxy $C_{1-6}$ alkylene, or halogeno;

$R_3$ is $C_{2-6}$ alkenyl, $C_{1-6}$ alkoxy, hydroxy $C_{1-6}$ alkyl, $C_{1-6}$ alkyl, or OH;

$R_4$ is H, $C_{1-6}$ alkyl, phenyl or benzyl;

$R_5$ is H, $C_{1-6}$ alkyl, OH, $C_{1-6}$ alkoxy,

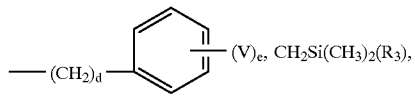

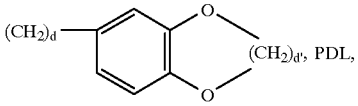

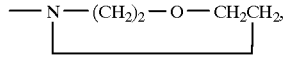

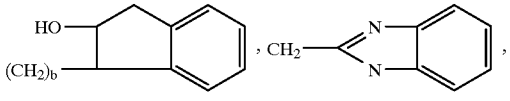

$-(C_{1-6}\text{ alkylene})OR_4$ or $-CH(Y)(Z)$,

Y being $C_{1-6}$ hydroxy alkylene, $C_{1-6}$ alkyl, or $(CH_2)_e\text{—}C_6H_4\text{—}(V)_a$, and Z being CHO, $CO_2R_4$, CONHR or $(CH_2)_e\text{—}OR_4$, and V being $OR_4$ or hydroxy $C_{1-6}$ alkylene, $R_6$ is as defined for $R_5$ with the proviso that $R_6$ is other than H when $R_5$ is H, and when $R_5$ and $R_6$ are taken together with nitrogen atom to which they are attached form a heterocyclic moiety of the formulae (a) —N(CH₂)₃CH₂, (b) —N(CH₂)₄CH₂, (c) —N(CH₂)₂OCH₂CH₂, (d) [structure: N-methyl tetrahydroisoquinoline with (CH₂)_b]

(e) [structure: R₃R₃Si-containing N-methyl pyrrolidine with R₇]

(f) [structure: decahydroisoquinoline with N-methyl and R₇]

(g) —N(CH₂)₂N—CH₂CH₂, with CH(O) substituent (h) —NCH₂C(=R₈)(CH₂)₂CH₂, or (i) —N(CH₂)₂CCH₂CH₂, with =R₈

R₇ is CH₂OR₄, C(O)NHR₄ or CHO,

R₈ is (H,OH) or =O;

a is zero, 1, 2 or 3;

b and b' are each independently zero or 1;

d and d' are each independently 1 or 2;

e and e' are each independently zero, 1 or 2; and x is zero or one.

2. The compound of claim 1 wherein x is one.

3. The compound of claim 2 wherein $P_1$ is $C_{1-3}$ alkylene—[phenyl ring with T and T' substituents].

4. The compound of claim 1 wherein b is 1.

5. The compound of claim 1 wherein T' is hydrogen.

6. The compound of claim 1 wherein b is 1, W is $C_{1-3}$ alkylene, and R is morpholinyl and T' is hydrogen.

7. The compound of claim 1 wherein b is 1, W is $C_{1-3}$ alkylene, and R is pyridyl and T' is hydrogen.

8. The compound of claim 1 wherein b is 1, W is $C_{1-3}$ alkylene, and R is ethenyl and T' is hydrogen.

9. The compound of claim 1 wherein W is $C_{1-2}$ alkylene.

10. The compound of claim 1 wherein $P_2$ is $C_{1-6}$ alkyl.

11. The compound of claim 1 wherein $P_2$ is $C_{1-3}$ alkyl.

12. The compound of claim 1 wherein $R_1$ is benzyloxy.

13. The compound of claim 1 wherein $R_1$ is PDL.

14. The compound of claim 1 wherein $R_5$ is H and $R_6$ is benzyl.

15. The compound of claim 1 wherein $R_5$ is H and $R_6$ is CH(Y)(Z) wherein Y is $C_{1-3}$ alkyl and Z is —(CH₂)_e—OR₄ wherein e is 1 and $R_4$ is benzyl or $C_{1-3}$ alkyl.

16. A process for preparing compound of the formula $$R_1\left[\begin{array}{c} P_2 \\ | \\ CNHCH \\ \| \\ O \end{array}\right]_x \begin{array}{c} P_1 \\ | \\ CNHCHC—CF_2C—NR_5R_6 \\ \| \quad \| \quad \| \\ O \quad O \quad O \end{array}$$  I and the hydrates, isostere and pharmaceutically acceptable salts thereof wherein $P_1$ is $C_{1-6}$ alkylene—[phenyl ring with T and T' substituents], wherein T is [(O)_b—W—R] and T' is [(O)_b'—W'—R'] or H, wherein each of W and W' are independently $C_{1-6}$ alkylene or nothing,
provided that W is $C_{2-6}$ alkylene when W is directly attached to a nitrogen atom in R,
provided that W' is $C_{2-6}$ alkylene when W' is directly attached to a nitrogen atom in R';

$P_2$ is $C_{1-6}$ alkyl, cyclopentyl, hydroxy $C_{1-6}$ alkyl, phenyl, benzyl or 3-tetrahydrofuryl;

R and R' are each independently $C_{2-6}$ alkenyl, piperazinyl, substituted piperazinyl, piperidyl, morpholinyl, pyridyl, pyrazinyl, or pyrimidinyl, wherein substituted piperazinyl is piperazinyl substituted on one nitrogen atom thereof with CHO, C(O)NHR₄, $C_{1-4}$ alkyl or CO₂R₄;

$R_1$ is benzyloxy, $C_{1-6}$ alkoxy, $C_{1-6}$ alkyl, phenyl, benzyl, phenethyl, fluorenylmethylenoxy, 2-quinolinyl, PDL,

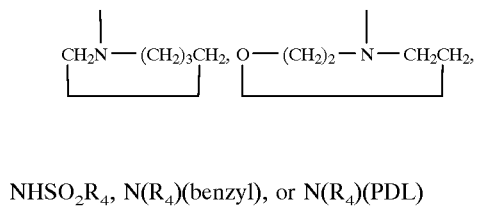

NHSO$_2$R$_4$, N(R$_4$)(benzyl), or N(R$_4$)(PDL)

PDL is —(CH$_2$)$_a$-2-, 3-, or 4-pyridyl, or p-substituted benzyloxy, wherein the substitution is with a nitro, OH, amino, C$_{1-6}$ alkoxy, hydroxy C$_{1-6}$ alkylene, or halogeno;

R$_3$ is C$_{2-6}$ alkenyl, C$_{1-6}$ alkoxy, hydroxy C$_{1-6}$ alkyl, C$_{1-6}$ alkyl, or OH;

R$_4$ is H, C$_{1-6}$ alkyl, phenyl or benzyl;

R is H, C$_{1-6}$ alkyl, OH, C$_{1-6}$ alkoxy,

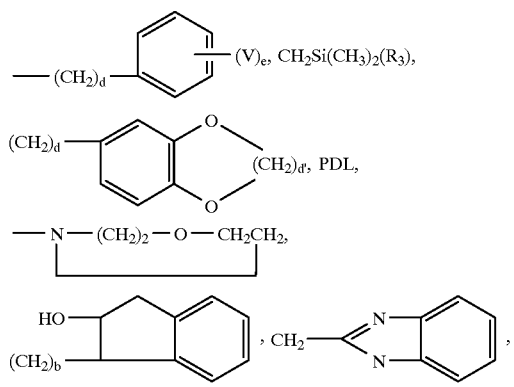

—(C$_{1-6}$ alkylene)—OR$_4$ or —CH(Y)(Z),

Y being C$_{1-6}$ hydroxy alkylene, C$_{1-6}$ alkyl, or (CH$_2$)$_e$—C$_6$H$_4$—(V)$_e$, and Z being CHO, CO$_2$R$_4$, CONHR$_4$ or (CH$_2$)$_e$—OR$_4$, and V being OR$_4$ or hydroxy C$_{1-6}$ alkylene, R$_6$ is as defined for R$_5$ with the proviso that R$_6$ is other than H when R$_5$ is H, and when R$_5$ and R$_6$ are taken together with nitrogen atom to which they are attached form a heterocyclic moiety of the formulae

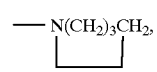 (a)

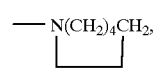 (b)

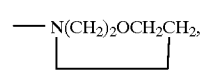 (c)

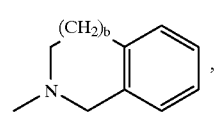 (d)

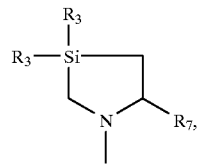 (e)

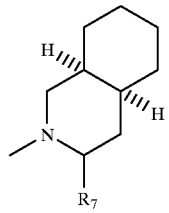 (f)

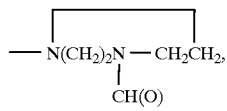 (g)

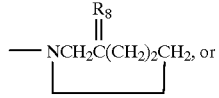 (h)

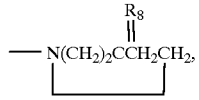 (i)

R$_7$ is CH$_2$OR$_4$, C(O)NHR$_4$ or CHO,

R$_8$ is (H,OH) or =O;

a is zero, 1, 2 or 3;

b and b' are each independently zero or 1;

d and d' are each independently 1 or 2;

e and e' are each independently zero, 1 or 2; and x is zero or one which comprises using a compound of the formula

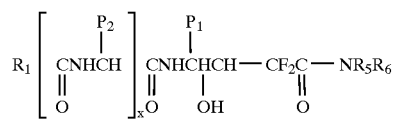

wherein R$_1$, P$_1$, P$_2$, R$_5$ and R$_6$ are defined above, oxidizing the compound and optionally converting the resulting oxidized compounds to a pharmaceutically acceptable salt thereof.

17. The process according to claim 16 wherein the oxidation step uses the Dess Martin oxidation.

18. The process according to claim 16 wherein the oxidation step uses the Swern oxidation.

19. A method of treating infection by the Human Immunodeficiency Virus in a patient in need of such therapy by administering to the patient a sufficient amount of the compound according to claim 1.

20. The method according to claim 19 wherein x is one.

21. The method according to claim 20 wherein $P_2$ is isopropyl, t-butyl, cyclopentyl or phenyl.

22. The method according to claim 20 wherein $P_1$ is 4-[(4-pyridyl)methyloxy]benzyl, 4-[(3-pyridyl)methyloxy]benzyl, 4-[(2-pyridyl)methyloxy]benzyl, 4-[2-(N-morpholyl)ethyloxy]benxyl, 4-[2-(N-piperidyl)ethyloxy]benzyl, or 4-pentenyl.

23. The method according to claim 20 wherein $R_1$ is benzyl, 3-pyridyl(ethyl), 2-pyridyl)ethyl), or N-morpholino.

24. The method according to claim 20 wherein $R_6$ is hydrogen and $R_5$ is benzyl, 2-pyridylmethyl, N-morpholino, 3-pyridylmethyl,

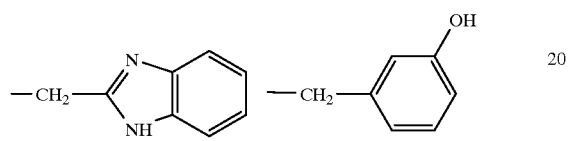

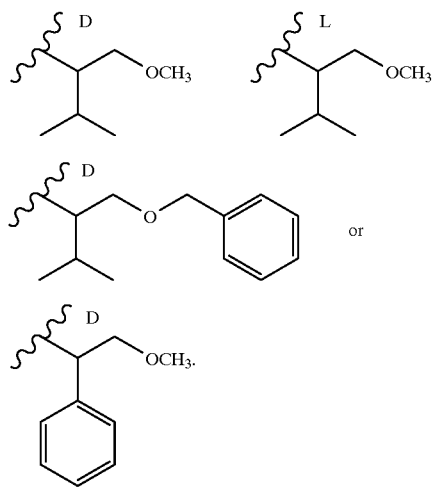

* * * * *

UNITED STATES PATENT AND TRADEMARK OFFICE
CERTIFICATE OF CORRECTION

PATENT NO. : 5,948,778

DATED : September 7, 1999

INVENTOR(S) : Viviane Van Dorsselaer, Daniel Schirlin and Céline Tarnus

It is certified that error appears in the above-indentified patent and that said Letters Patent is hereby corrected as shown below:

Column 2, Line 25 reads as "$(R_3)_2$, and should read as --$(R_3)$,--.

Column 11, Line 34 reads as "undirectly" and should read as --indirectly--.

Column 22, Line 14 reads as "alcool" and should read as --alcohol--.

Column 22, Line 40 reads as "in vacuo a residue" and should read as

--*in vacuo* afforded a residue--.

Column 25, Line 27 reads as "an hydrogen" and should read as --a hydrogen--.

Column 28, Line 29 reads as "These impure material has been" and should read as

--These impure materials have been--.

Column 28, Line 53 reads as "individuals molecules" and should read as

--individual molecules--.

Column 28, Line 59 reads as "Biochemichal" and should read as --Biochemical--.

Column 29, Line 11 reads as "steriel" and should read as --sterile--.

Column 31, within the table, Column $P_1$, item 12, reads as "(N-morpholyl)" and should read as --(N-piperidyl)--.

Column 36, Line 60 reads as "$(V)_a$" and should read as --$(V)_e$--.

Column 39, Line 20 reads as "R is" and should read as --$R_5$ is--.

UNITED STATES PATENT AND TRADEMARK OFFICE
CERTIFICATE OF CORRECTION

PATENT NO. : 5,948,778

DATED : September 7, 1999

INVENTOR(S) : Viviane Van Dorsselaer, Daniel Schirlin and Celine Tarnus

It is certified that error appears in the above-indentified patent and that said Letters Patent is hereby corrected as shown below:

Column 41, Line 8 reads as "benxyl" and should read as --benzyl--.

Signed and Sealed this

Seventeenth Day of April, 2001

*Attest:*

NICHOLAS P. GODICI

*Attesting Officer*   Acting Director of the United States Patent and Trademark Office